United States Patent
Ma et al.

(10) Patent No.: US 9,676,767 B2
(45) Date of Patent: Jun. 13, 2017

(54) INDOLOACRIDINE-CONTAINING DERIVATIVE, PREPARATION PROCESS AND USE THEREOF, AND ORGANIC LUMINESCENT DEVICE

(71) Applicants: BOE TECHNOLOGY GROUP CO., LTD., Beijing (CN); JiLin OLED Material Tech Co., Ltd., Changchun, Jilin Province (CN)

(72) Inventors: Wenyu Ma, Beijing (CN); Xiaoyu Ma, Beijing (CN); Hui Wang, Beijing (CN); Na Li, Beijing (CN)

(73) Assignees: BOE TECHNOLOGY GROUP CO., LTD., Beijing (CN); JILIN OLED MATERIAL TECH CO., LTD., Changchun, Jilin Province (CN)

( * ) Notice: Subject to any disclaimer, the term of this patent is extended or adjusted under 35 U.S.C. 154(b) by 306 days.

(21) Appl. No.: 14/425,254

(22) PCT Filed: May 30, 2014

(86) PCT No.: PCT/CN2014/078910
§ 371 (c)(1),
(2) Date: Mar. 2, 2015

(87) PCT Pub. No.: WO2015/085728
PCT Pub. Date: Jun. 18, 2015

(65) Prior Publication Data
US 2016/0046621 A1 Feb. 18, 2016

(30) Foreign Application Priority Data
Dec. 10, 2013 (CN) .......................... 2013 1 0666477

(51) Int. Cl.
*C07D 471/04* (2006.01)
*H01L 51/00* (2006.01)
*C07D 475/00* (2006.01)
*C07D 519/00* (2006.01)
*C09K 11/06* (2006.01)
*H01L 51/50* (2006.01)

(52) U.S. Cl.
CPC .......... *C07D 471/04* (2013.01); *C07D 475/00* (2013.01); *C07D 519/00* (2013.01); *C09K 11/06* (2013.01); *H01L 51/0052* (2013.01); *H01L 51/0067* (2013.01); *H01L 51/0072* (2013.01); *C09K 2211/1074* (2013.01); *H01L 51/006* (2013.01); *H01L 51/0059* (2013.01); *H01L 51/0085* (2013.01); *H01L 51/5016* (2013.01); *H01L 51/5056* (2013.01); *H01L 51/5088* (2013.01); *H01L 2251/308* (2013.01)

(58) Field of Classification Search
None
See application file for complete search history.

(56) References Cited

U.S. PATENT DOCUMENTS

| 2011/0114927 A1 | 5/2011 | Obana et al. |
| 2016/0359120 A1* | 12/2016 | Li .................. H01L 51/0084 |
| 2016/0359125 A1* | 12/2016 | Li .................. H01L 51/0087 |

FOREIGN PATENT DOCUMENTS

| CN | 103189469 A | 7/2013 |
| CN | 103788088 A | 5/2014 |
| JP | 2008120786 A | 5/2008 |
| JP | 2010183072 A | 8/2010 |
| KR | 20110102055 A | 9/2011 |

OTHER PUBLICATIONS

English translation of first Chinese Office Action dated Feb. 13, 2015, for corresponding Chinese Application No. 201310666477.9.
International Search Report and Written Opinion in Chinese dated Aug. 8, 2014, for PCT/CN2014/078910.

* cited by examiner

Primary Examiner — Robert S Loewe
(74) Attorney, Agent, or Firm — Kinney & Lange, P.A.

(57) ABSTRACT

The disclosure provides an indoloacridine-containing derivative represented by formula (I), wherein A is a group represented by formula (II), and wherein X, Y, Z and W represent a carbon atom or a nitrogen atom, and at least one of W, X, Y and Z represent a nitrogen atom; R represents a phenyl group, a biphenylyl group, a naphthyl group or a phenanthryl group. The disclosure further provides a process for preparing the compound. The disclosure further provides an organic electroluminescent device comprising the compound. This compound can be used as a phosphorescence host material, a hole-injecting material or a hole-transporting material in an organic electroluminescent device.

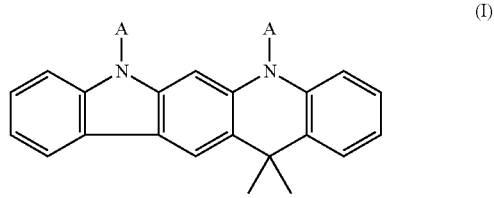

(I)

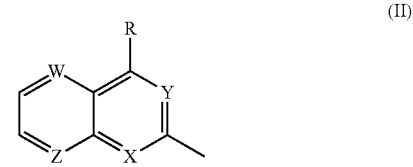

(II)

14 Claims, No Drawings

INDOLOACRIDINE-CONTAINING DERIVATIVE, PREPARATION PROCESS AND USE THEREOF, AND ORGANIC LUMINESCENT DEVICE

TECHNICAL FIELD

The disclosure relates to the field of organic photoelectric materials, especially, to an indoloacridine-containing derivative, the preparation process and use thereof, and an organic luminescent device.

BACKGROUND

An organic electroluminescent (EL) device (hereinafter, briefly referred to as "organic EL device") is generally composed of two opposite electrodes and at least one layer of an organic light-emitting compound inserted between these two electrodes. Electric charges are injected into the organic layer formed between the anode and the cathode to form electron hole pairs, so that the organic compound having fluorescent or phosphorescent characteristics generates light emission.

The research on the organic EL material started from 1950, beginning with the observation of Bernanose on an organic pigment-containing polymeric thin film to which high current and voltage was applied. In 1965, Pope et al. for the first time discovered the electroluminescent property of anthracene single crystal, which is the first example of the electroluminescence of organic compounds. In 1987, Tang et al. from Kodak Company discovered that even at a low voltage of 10V or less, an organic luminescent device, which is formed from an organic material and has laminated separate functional layers, can provide a high luminance of 1000 cd/cm$^2$ or more.

In an organic material, the hole mobility is significantly higher than the electron mobility, so holes and electrons can be more effectively transported to the light-emitting layer when a hole transport layer and an electron transport layer are properly used. Additionally, when a balance between the hole density and the electron density in the light-emitting layer is achieved, the luminous efficiency can be improved.

When an electron and a hole recombine in an organic molecule, due to different manners of electron spin symmetry, two forms of excited state will occur. One is the form of a singlet excited state formed by a ground state electron with asymmetric spin, which releases energy in the form of fluorescence and then returns to the ground state; the other is the form of a triplet excited state formed by a ground state electron with symmetric spin, which releases energy in the form of phosphorescence and then returns to the ground state. According to theoretical speculation, the ratio of the singlet excited state to the triplet excited state caused by the recombination of electric charges is 1:3. If the energy of the singlet excited state is transferred to the triplet excited state for emitting phosphorescence, the internal quantum efficiency thereby may be close to 100%.

Generally, the phosphorescence host luminescent materials such as the carbazole ring compounds (e.g. CBP, etc.), and the phosphorescence guest luminescent materials such as a compound attached with iridium (Ir), platinum (Pt) or the like as a central metal atom, are widely used.

SUMMARY

The disclosure is to solve the ultimate technical problem, and provides a compound which may be used as a host material for red phosphorescence, a hole-injecting material or a hole-transporting material. The compound has an improved electrical stability, a better charge-transporting capability, a high glass transition temperature and does not crystallize. The material can be used for producing an organic electroluminescent (EL) device comprising an indoloacridine-containing derivative which has a high efficiency, a high luminance, a long lifetime and a high stability The disclosure further provides an organic electroluminescent (EL) device comprising the compound of the disclosure which has a low voltage, a high efficiency, a high luminance, a long lifetime and a high stability.

The present disclosure provides an indoloacridine-containing derivative represented by formula (I):

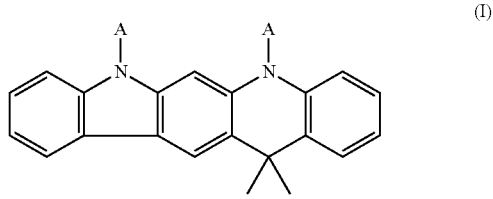

(I)

wherein A is a quinoline derivative group-containing compound represented by formula (II):

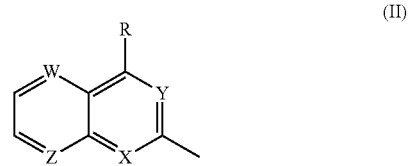

(II)

wherein X, Y, Z and W represent a carbon atom or a nitrogen atom, and at least one of W, X, Y and Z represents a nitrogen atom; R represents a phenyl group, a biphenylyl group, a naphthyl group or a phenanthryl group. Preferably, X represents a nitrogen atom. More preferably, X and Y represent a nitrogen atom. Even more preferably, X, Y and Z represent a nitrogen atom. Still more preferably, X, Y, Z and W represent a nitrogen atom. Preferably, R represents phenyl, 1-naphthyl, 2-naphthyl, 4-biphenylyl, 3-biphenylyl or 9-phenanthryl.

A preferable example of the organic electroluminescent material in the disclosure, which is an indoloacridine-containing derivative, is any one selected from the compounds represented by the formulae 1-24 in the following Table 1.

TABLE 1

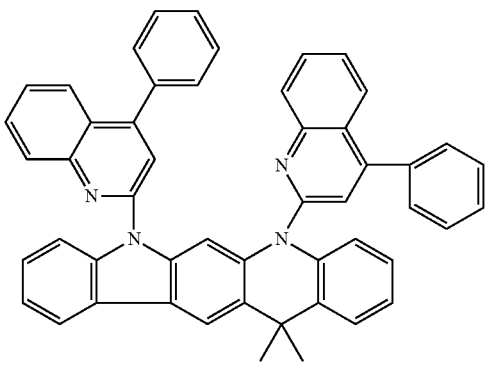 [SMILES: CC1(C)c2ccccc2N(c2cc(-c3ccccc3)c3ccccc3n2)c2cc3c(cc21)c1ccccc1n3-c1cc(-c2ccccc2)c2ccccc2n1]

1

TABLE 1-continued
2
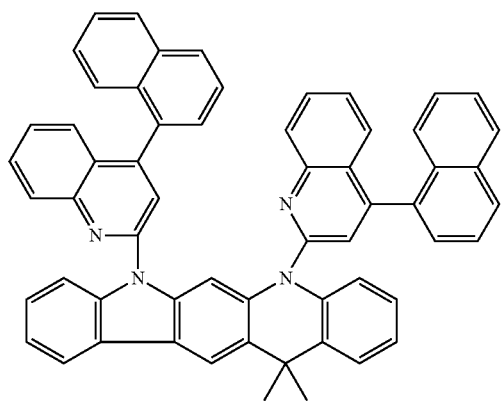
3
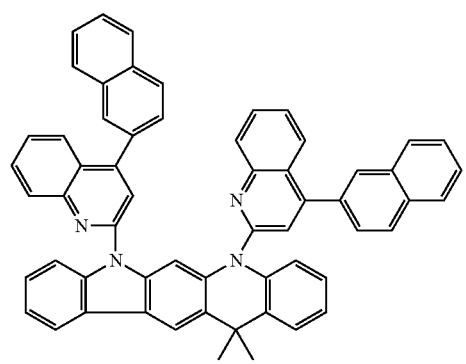 [SMILES: CC1(C)c2ccccc2N(c2cc(-c3ccc4ccccc4c3)c3ccccc3n2)c2cc3c(cc21)c1ccccc1n3-c1cc(-c2ccc3ccccc3c2)c2ccccc2n1]
4
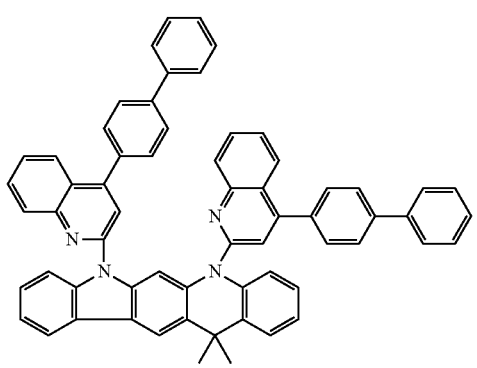 [SMILES: CC1(C)c2ccccc2N(c2cc(-c3ccc(-c4ccccc4)cc3)c3ccccc3n2)c2cc3c(cc21)c1ccccc1n3-c1cc(-c2ccc(-c3ccccc3)cc2)c2ccccc2n1]
5
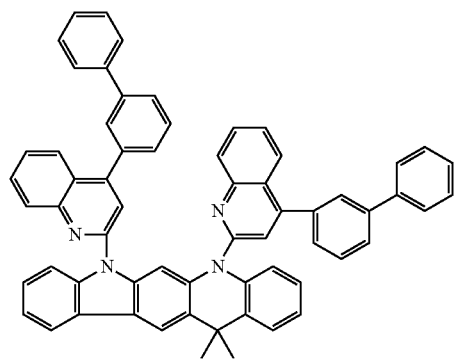 [SMILES: CC1(C)c2ccccc2N(c2cc(-c3cccc(-c4ccccc4)c3)c3ccccc3n2)c2cc3c(cc21)c1ccccc1n3-c1cc(-c2cccc(-c3ccccc3)c2)c2ccccc2n1]
TABLE 1-continued
6
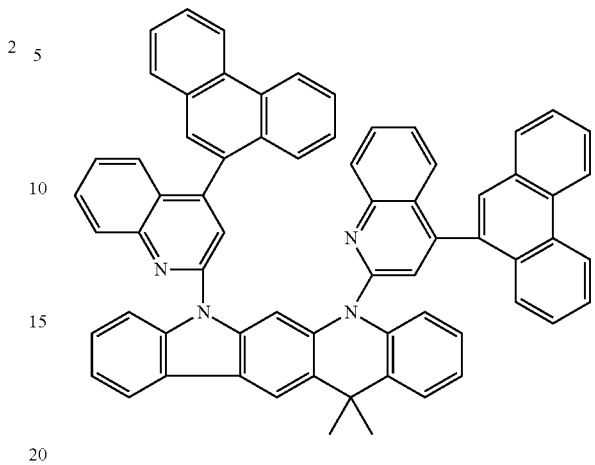
7
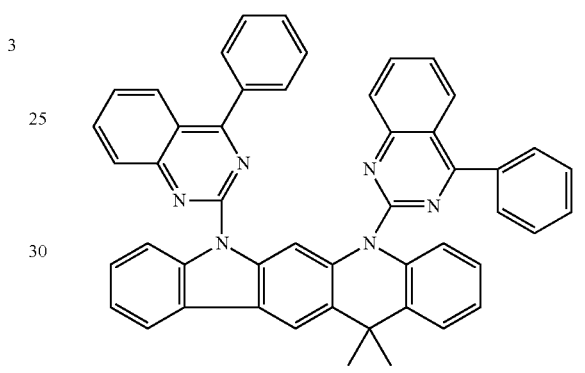
8
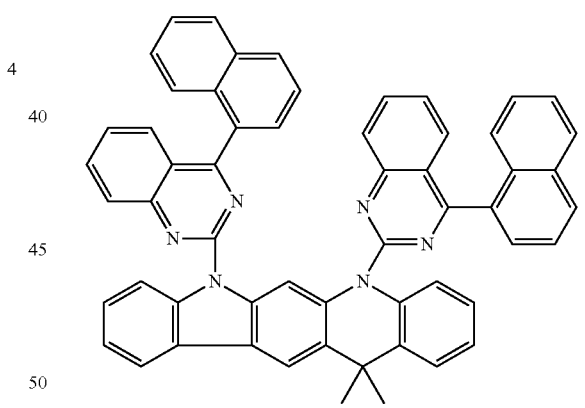
9
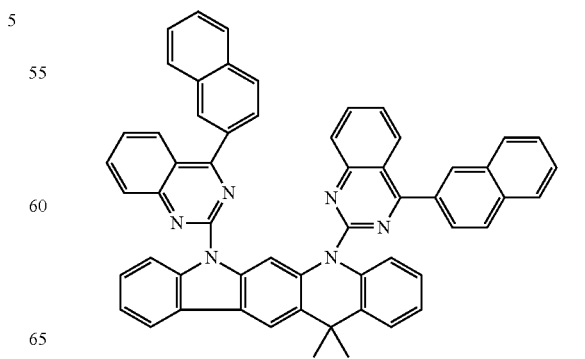

TABLE 1-continued
10
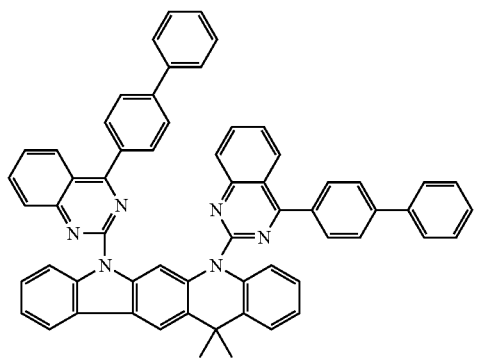 [SMILES: CC1(C)c2ccccc2N(c2nc(-c3ccc(-c4ccccc4)cc3)c3ccccc3n2)c2cc3c(cc21)c1ccccc1n3-c1nc(-c2ccc(-c3ccccc3)cc2)c2ccccc2n1]
11
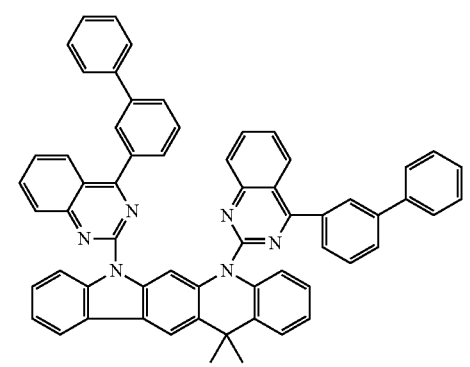 [SMILES: CC1(C)c2ccccc2N(c2nc(-c3cccc(-c4ccccc4)c3)c3ccccc3n2)c2cc3c(cc21)c1ccccc1n3-c1nc(-c2cccc(-c3ccccc3)c2)c2ccccc2n1]
12
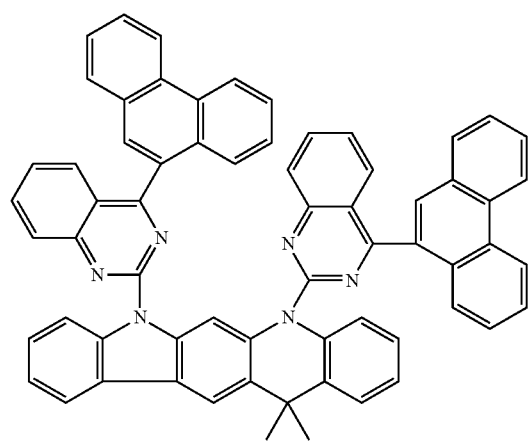 [SMILES: CC1(C)c2ccccc2N(c2nc(-c3cc4ccccc4c4ccccc34)c3ccccc3n2)c2cc3c(cc21)c1ccccc1n3-c1nc(-c2cc3ccccc3c3ccccc23)c2ccccc2n1]
13
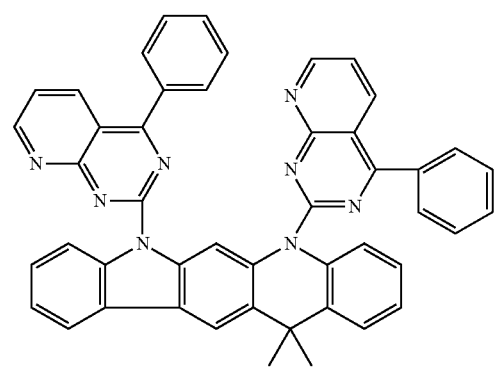
TABLE 1-continued
14
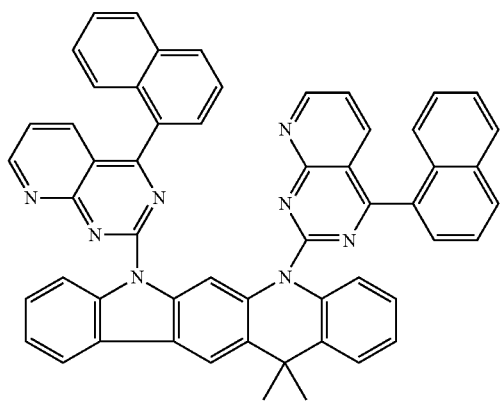 [SMILES: CC1(C)c2ccccc2N(c2nc(-c3cccc4ccccc34)c3cccnc3n2)c2cc3c(cc21)c1ccccc1n3-c1nc(-c2cccc3ccccc23)c2cccnc2n1]
15
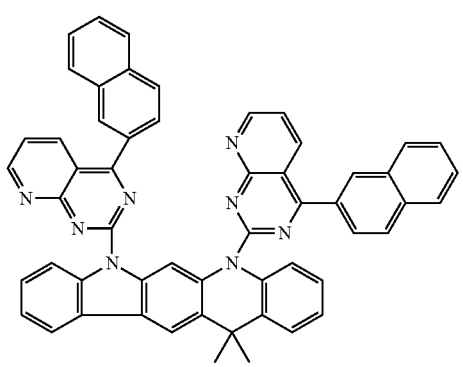 [SMILES: CC1(C)c2ccccc2N(c2nc(-c3ccc4ccccc4c3)c3cccnc3n2)c2cc3c(cc21)c1ccccc1n3-c1nc(-c2ccc3ccccc3c2)c2cccnc2n1]
16
17

TABLE 1-continued
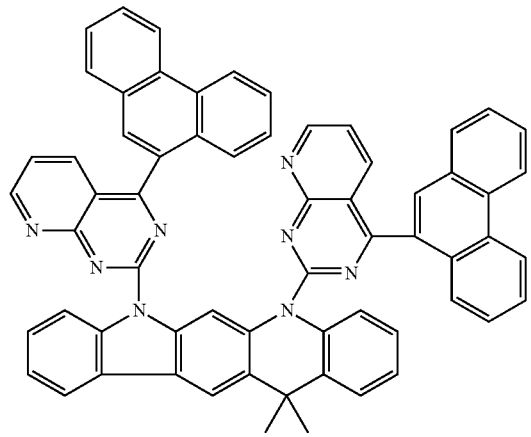 [SMILES: CC1(C)c2ccccc2N(c2nc(-c3cc4ccccc4c4ccccc34)c3cccnc3n2)c2cc3c(cc21)c1ccccc1n3-c1nc(-c2cc3ccccc3c3ccccc23)c2cccnc2n1]
18
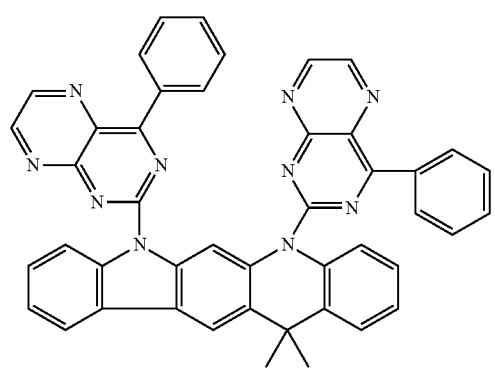
19
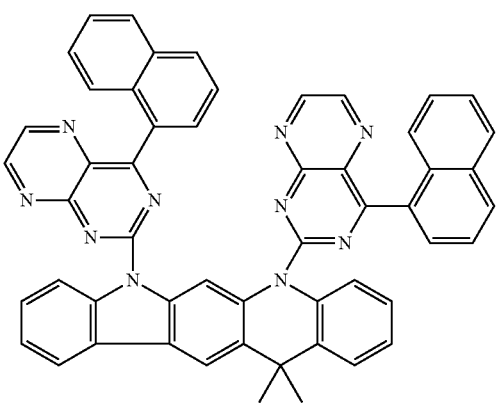 [SMILES: CC1(C)c2ccccc2N(c2nc(-c3cccc4ccccc34)c3nccnc3n2)c2cc3c(cc21)c1ccccc1n3-c1nc(-c2cccc3ccccc23)c2nccnc2n1]
20
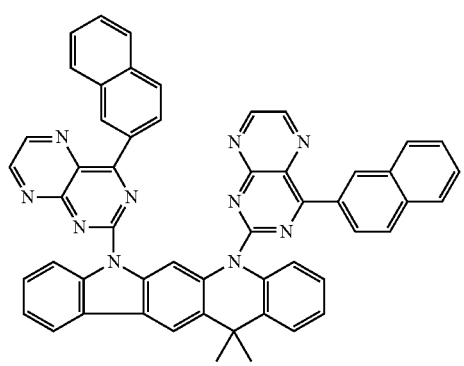
21
TABLE 1-continued
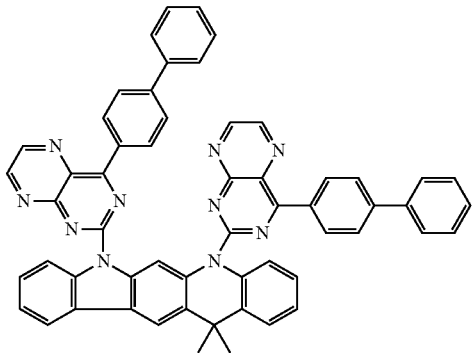 [SMILES: CC1(C)c2ccccc2N(c2nc(-c3ccc(-c4ccccc4)cc3)c3nccnc3n2)c2cc3c(cc21)c1ccccc1n3-c1nc(-c2ccc(-c3ccccc3)cc2)c2nccnc2n1]
22
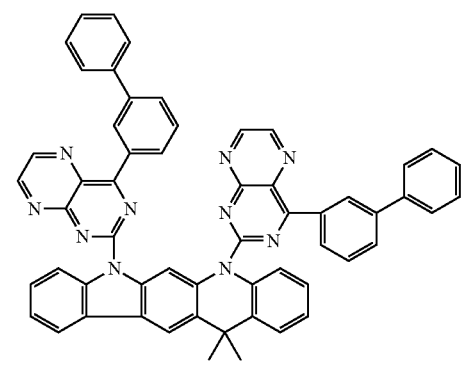
23
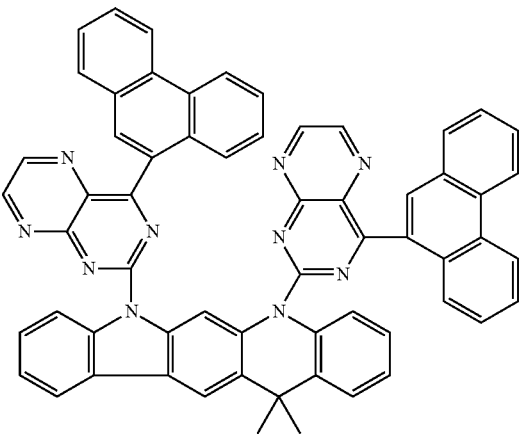 [SMILES: CC1(C)c2ccccc2N(c2nc(-c3cc4ccccc4c4ccccc34)c3nccnc3n2)c2cc3c(cc21)c1ccccc1n3-c1nc(-c2cc3ccccc3c3ccccc23)c2nccnc2n1]
24
The disclosure further provides a process for preparing the indoloacridine-containing derivative represented by formula (I), comprising a step of reacting a compound represented by formula (III)
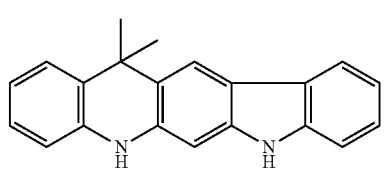
(III)

with a compound represented by formula (IV)

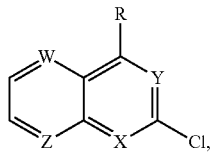

(IV)

wherein R, X, Y, Z and W have the same definitions as those in formula (II).

Preferably, the production process includes the following Steps S1 to S3:

Step S1: adding the compound represented by formula (III), the compound represented by formula (IV), potassium hydroxide, copper iodide and a solvent into a degassed reaction container;

Step S2: increasing the reaction temperature and refluxing, allowing the reaction to be carried out sufficiently;

Step S3: performing filtration, washing and recrystallization to obtain the compound represented by formula (I).

The compound represented by formula (III) is 13,13-dimethyl-7,13-dihydro-5H-indoloacridine.

The process for producing the compound represented by formula (I) may comprise performing the following Steps M1 to M5 to produce the compound represented by formula (III):

Step M1: reacting 9,10-dihydro-9,9-dimethylacridine with solid triphosgene to obtain a compound represented by formula (V):

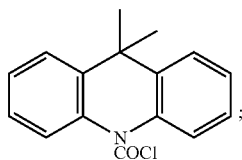

(V)

Step M2: reacting the compound represented by formula (V) with N-bromosuccinimide to obtain a compound represented by formula (VI):

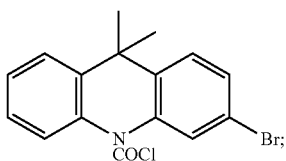

(VI)

Step M3: reacting the compound represented by formula (VI) with 2-chloroaniline to obtain a compound represented by formula (VII):

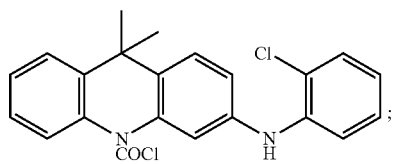

(VII)

Step M4: reacting the compound represented by formula (VII) in the presence of palladium acetate, di-tert-butyl methylphosphonium tetraphenylborate and cesium carbonate, to obtain a compound represented by formula (VIII):

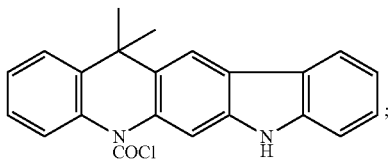

(VIII)

Step M5: removing the chloroformyl protection of the compound represented by formula (VIII) to obtain the compound represented by formula (III).

The process for preparing the compound represented by formula (I) may comprise producing the compound represented by formula (IV) by reacting R—B(OH)$_2$ with a compound represented by formula (IX):

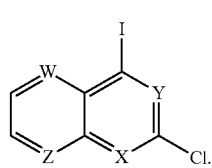

(IX)

Preferably, the compound represented by formula (IV) is obtained by the following Steps N1 to N3:

Step N1: adding the compound represented by formula (IX), R—B(OH)$_2$, potassium carbonate and a solvent into a degassed reaction container;

Step N2: refluxing, allowing the reaction to be carried out sufficiently;

Step N3: obtaining the compound represented by formula (IV) by performing extraction, washing, drying and purification with column chromatography. This compound can be directly used for producing the compound represented by formula (I).

The disclosure further provides an organic electroluminescent device, comprising a first electrode, a second electrode and one or more organic compound layer(s) provided between the first electrode and the second electrode, wherein at least one organic compound layer comprises at least one compound represented by formula (I). Preferably, the compound represented by formula (I) is a phosphorescence host material.

The disclosure further provides use of the compound represented by formula (I) as a phosphorescence host material, a hole-injecting material or a hole-transporting material in an organic electroluminescent device.

The disclosure provides an indoloacridine-containing derivative, the preparation process and its use in an organic electroluminescent device. The indoloacridine-containing derivative has high luminescence efficiency. High luminescence efficiency indicates that the compound can be used as a luminescent material or a luminescent host material, especially as a red phosphorescence host material used in an organic electroluminescent device. It has a high glass transition temperature and does not crystallize easily. The organic electroluminescent device using the indoloacridine-containing derivative exhibits a high efficiency, a high luminance, a long lifetime, and has the advantage of lower manufacturing cost. Additionally, the lifetime of the organic electroluminescent device is prolonged and the manufacturing cost of the organic electroluminescent device is reduced.

DETAILED DESCRIPTION

The present disclosure provides an indoloacridine-containing derivative represented by formula (I):

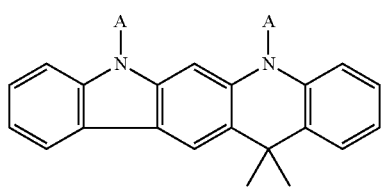

(I)

wherein A is a quinoline derivative group-containing compound represented by formula (II):

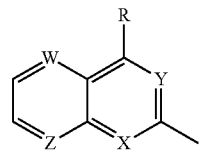

(II)

wherein X, Y, Z and W represent a carbon atom or a nitrogen atom, and at least one of W, X, Y and Z represents a nitrogen atom; R represents a phenyl group, a biphenyl group, a naphthyl group or a phenanthryl group. Preferably, X represents a nitrogen atom. More preferably, X and Y represent a nitrogen atom. Even more preferably, X, Y and Z represent a nitrogen atom. Still more preferably, X, Y, Z and W represent a nitrogen atom. Preferably, R represents phenyl, 1-naphthyl, 2-naphthyl, 4-biphenylyl, 3-biphenylyl or 9-phenanthryl.

A preferable example of the organic electroluminescent material in the disclosure, which is an indoloacridine-containing derivative, is any one selected from the compounds represented by the formulae 1-24 in the following Table 1:

TABLE 1

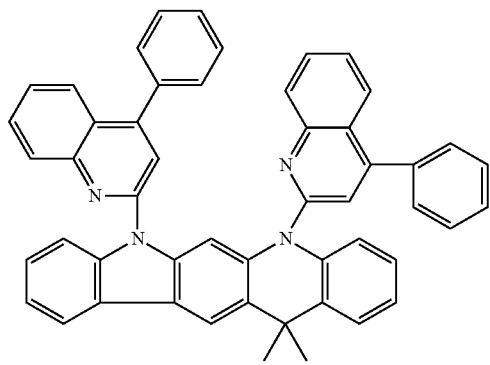 [SMILES: CC1(C)c2ccccc2N(c2cc(-c3ccccc3)c3ccccc3n2)c2cc3c(cc21)c1ccccc1n3-c1cc(-c2ccccc2)c2ccccc2n1]

1

TABLE 1-continued

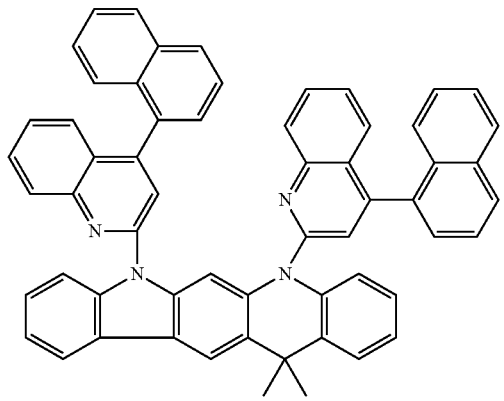 [SMILES: CC1(C)c2ccccc2N(c2cc(-c3cccc4ccccc34)c3ccccc3n2)c2cc3c(cc21)c1ccccc1n3-c1cc(-c2cccc3ccccc23)c2ccccc2n1]

2

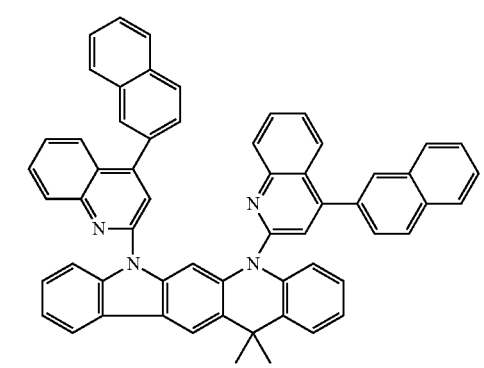 [SMILES: CC1(C)c2ccccc2N(c2cc(-c3ccc4ccccc4c3)c3ccccc3n2)c2cc3c(cc21)c1ccccc1n3-c1cc(-c2ccc3ccccc3c2)c2ccccc2n1]

3

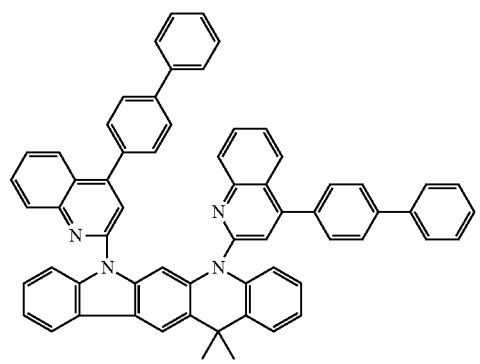

4

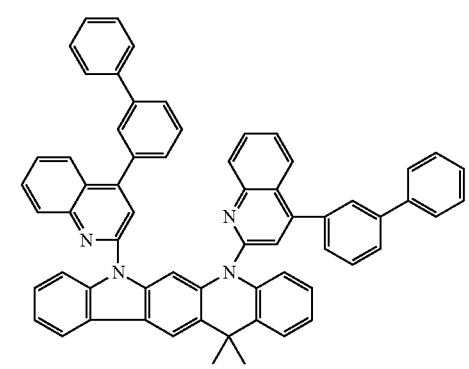 [SMILES: CC1(C)c2ccccc2N(c2cc(-c3cccc(-c4ccccc4)c3)c3ccccc3n2)c2cc3c(cc21)c1ccccc1n3-c1cc(-c2cccc(-c3ccccc3)c2)c2ccccc2n1]

5

TABLE 1-continued
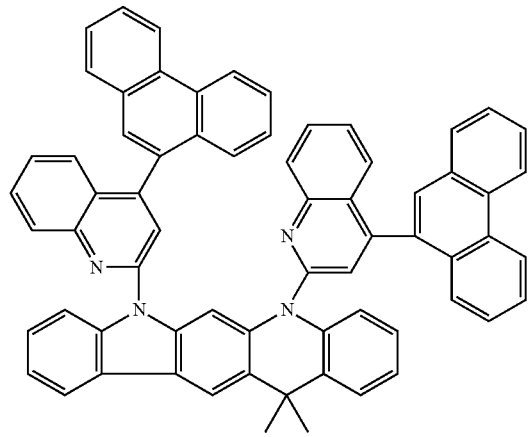
6
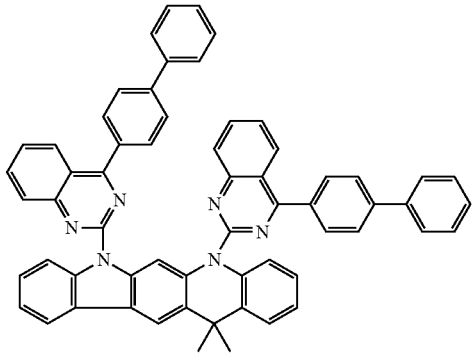
10
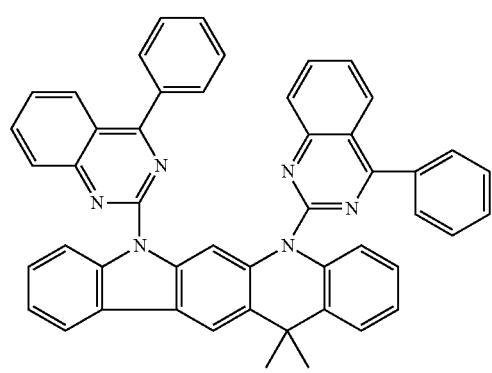 [SMILES: CC1(C)c2ccccc2N(c2nc(-c3ccccc3)c3ccccc3n2)c2cc3c(cc21)c1ccccc1n3-c1nc(-c2ccccc2)c2ccccc2n1]
7
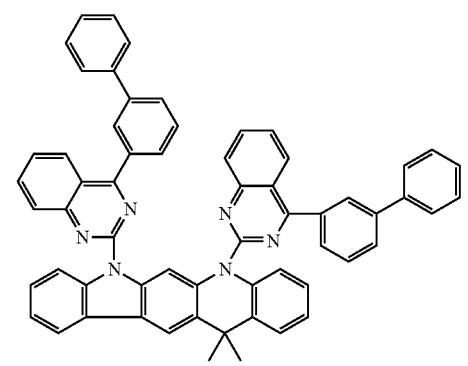 [SMILES: CC1(C)c2ccccc2N(c2nc(-c3cccc(-c4ccccc4)c3)c3ccccc3n2)c2cc3c(cc21)c1ccccc1n3-c1nc(-c2cccc(-c3ccccc3)c2)c2ccccc2n1]
11
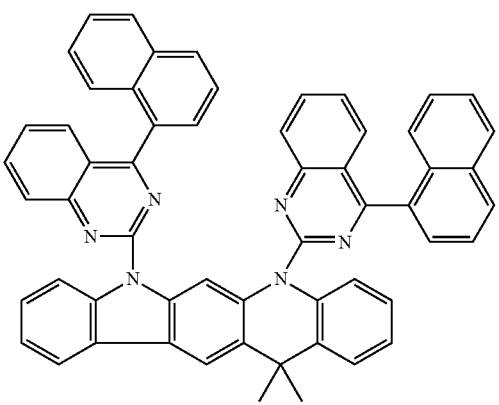
8
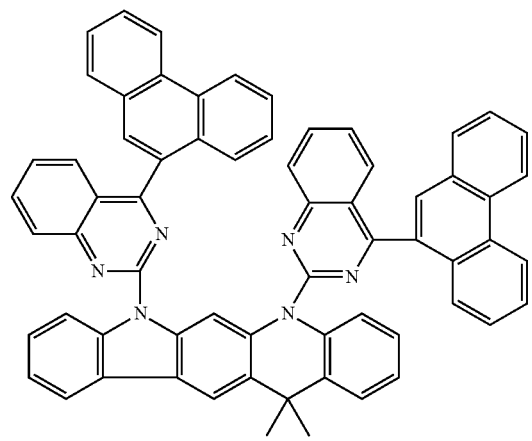 [SMILES: CC1(C)c2ccccc2N(c2nc(-c3cc4ccccc4c4ccccc34)c3ccccc3n2)c2cc3c(cc21)c1ccccc1n3-c1nc(-c2cc3ccccc3c3ccccc23)c2ccccc2n1]
12
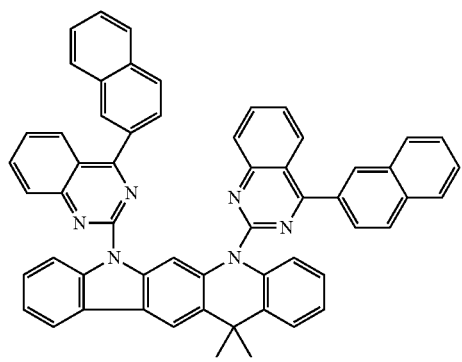
9
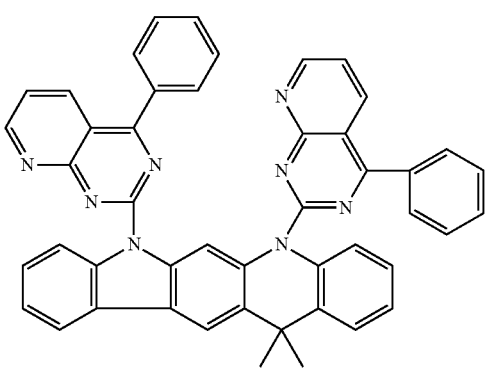
13

TABLE 1-continued
14
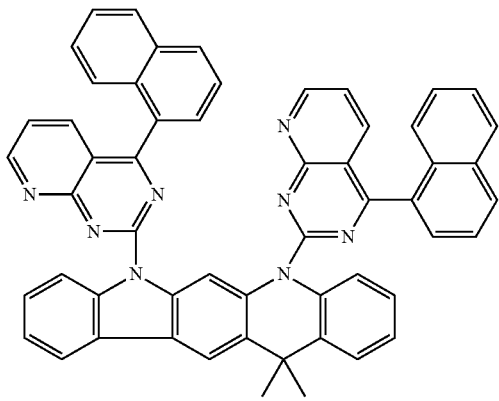
15
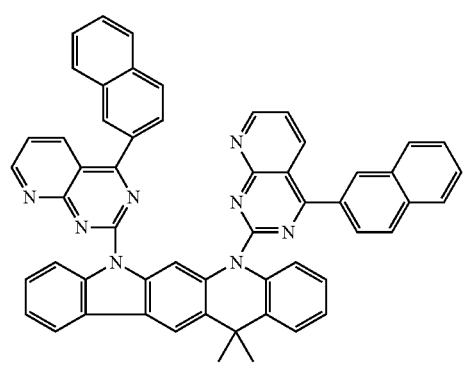 [SMILES: CC1(C)c2ccccc2N(c2nc(-c3ccc4ccccc4c3)c3cccnc3n2)c2cc3c(cc21)c1ccccc1n3-c1nc(-c2ccc3ccccc3c2)c2cccnc2n1]
16
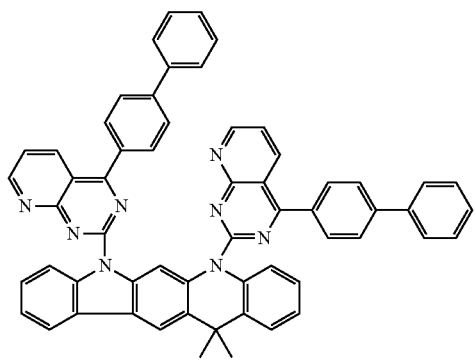
17
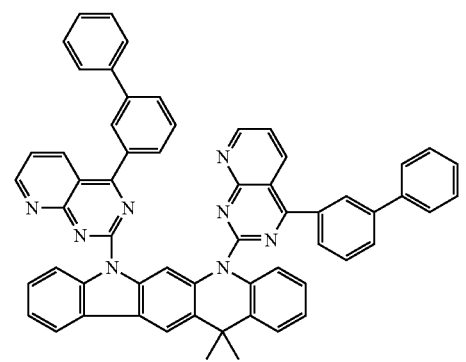 [SMILES: CC1(C)c2ccccc2N(c2nc(-c3cccc(-c4ccccc4)c3)c3cccnc3n2)c2cc3c(cc21)c1ccccc1n3-c1nc(-c2cccc(-c3ccccc3)c2)c2cccnc2n1]
TABLE 1-continued
18
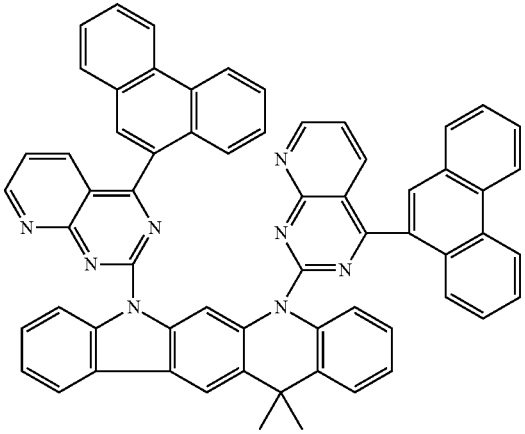 [SMILES: CC1(C)c2ccccc2N(c2nc(-c3cc4ccccc4c4ccccc34)c3cccnc3n2)c2cc3c(cc21)c1ccccc1n3-c1nc(-c2cc3ccccc3c3ccccc23)c2cccnc2n1]
19
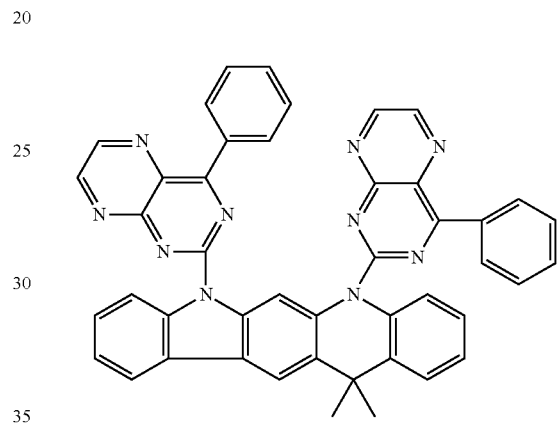
20
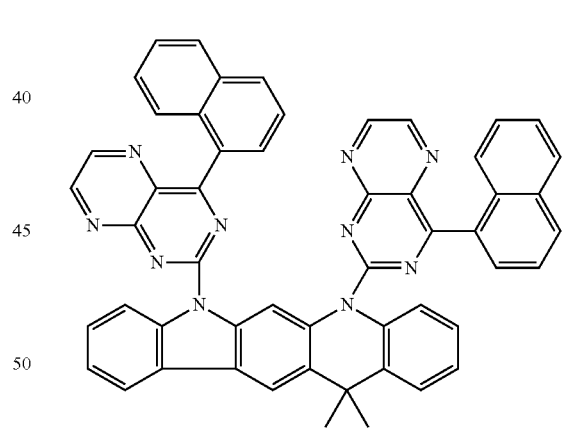
21
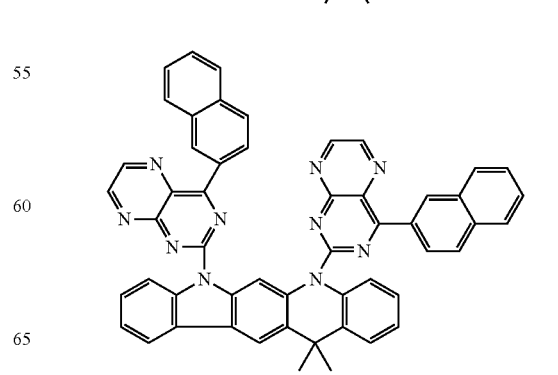

TABLE 1-continued

| | |
|---|---|
| 22 | 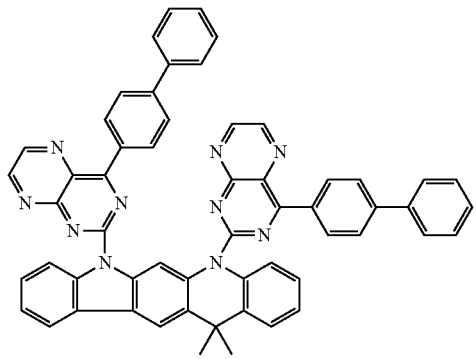 [SMILES: CC1(C)c2ccccc2N(c2nc(-c3ccc(-c4ccccc4)cc3)c3nccnc3n2)c2cc3c(cc21)c1ccccc1n3-c1nc(-c2ccc(-c3ccccc3)cc2)c2nccnc2n1] |
| 23 | 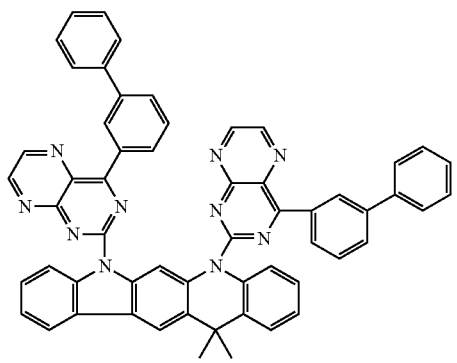 [SMILES: CC1(C)c2ccccc2N(c2nc(-c3cccc(-c4ccccc4)c3)c3nccnc3n2)c2cc3c(cc21)c1ccccc1n3-c1nc(-c2cccc(-c3ccccc3)c2)c2nccnc2n1] |
| 24 | 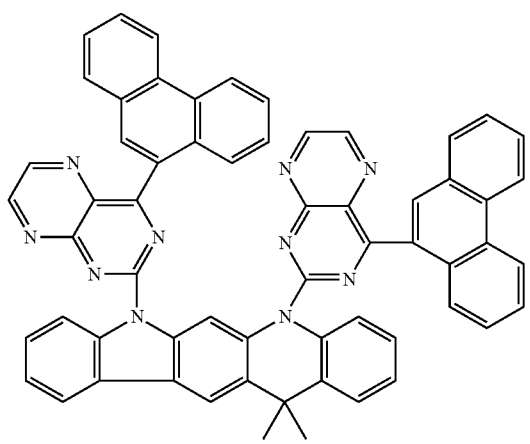 |

The disclosure further provides a process for preparing the indoloacridine-containing derivative represented by formula (I), comprising a step of reacting a compound represented by formula (III)

(III)

with a compound represented by formula (IV)

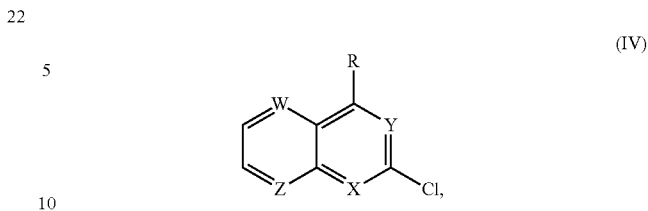

wherein R, X, Y, Z and W have the same definitions as those in formula (II).

Preferably, the production process includes the following Steps S1 to S3:

Step S1: adding the compound represented by formula (III), the compound represented by formula (IV), potassium hydroxide, copper iodide and a solvent into a degassed reaction container;

Step S2: increasing the reaction temperature and refluxing, allowing the reaction to be carried out sufficiently;

Step S3: performing filtration, washing and recrystallization to obtain the compound represented by formula (I).

More specifically, the compound represented by formula (IV), the compound represented by formula (III), copper iodide, potassium hydroxide, 8-hydroxyquinoline and dimethyl sulfoxide are heated and stirred under nitrogen atmosphere. After the reaction has been completed, methanol is added thereto at normal temperature. After filtration, washing and recrystallization are performed, the indoloacridine-containing derivative represented by formula (I) is obtained.

The compound represented by formula (III) is 13,13-dimethyl-7,13-dihydro-5H-indoloacridine.

The process for producing the compound represented by formula (I) may comprise performing the following Steps M1 to M5 to produce the compound represented by formula (III):

Step M1: reacting 9,10-dihydro-9,9-dimethylacridine with solid triphosgene to obtain a dimethylacridine compound protected by chloroformyl, which is represented by formula (V):

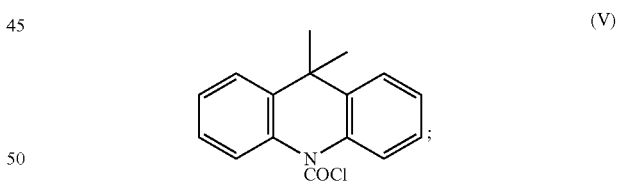

Step M2: reacting the compound represented by formula (V) with N-bromosuccinimide to obtain a dimethylacridine bromide protected by chloroformyl, which is represented by formula (VI):

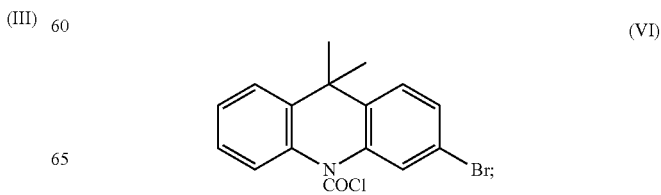

Step M3: reacting the compound represented by formula (VI) with 2-chloroaniline to obtain a chlorophenyl dimethylacridineamine compound protected by chloroformyl, which is represented by formula (VII):

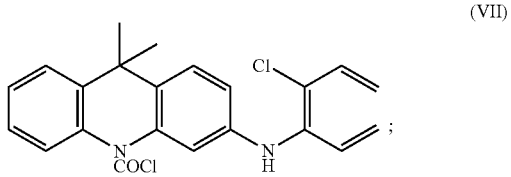

(VII)

Step M4: reacting the compound represented by formula (VII) in the presence of palladium acetate, di-tert-butyl methylphosphonium tetraphenylborate and cesium carbonate, to obtain a dimethylacridinoindole compound protected by chloroformyl, which is represented by formula (VIII):

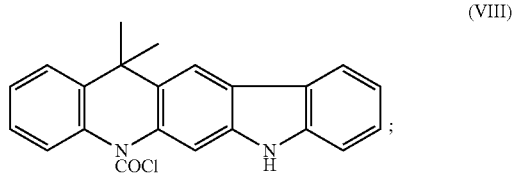

(VIII)

Step M5: removing the chloroformyl protection of the compound represented by formula (VIII) to obtain the compound 13,13-dimethyl-7,13-dihydro-5H-indoloacridine represented by formula (III).

More specifically, the following steps M1 to M5 are performed:

step M1: adding 9,10-dihydro-9,9-dimethylacridine, solid triphosgene and toluene into a reaction container, heating them to reflux, and performing washing, filtration and drying after the reaction is completed to obtain the compound represented by formula (V);

step M2: dissolving the compound represented by formula (V) in a solvent, adding a solution of N-bromosuccinimide under stirring at 0° C., and performing washing, drying and purification after the reaction is completed to obtain the compound represented by formula (VI);

step M3: dissolving the above-mentioned compound represented by formula (VI), along with 2-chloroaniline, palladium acetate, tri-tert-butylphosphine and cesium carbonate, in a solvent, stirring them at 120° C., allowing the reaction to be carried out sufficiently, and then performing washing, drying and purification to obtain the compound represented by formula (VII);

step M4: dissolving the compound represented by formula (VII), along with palladium acetate, di-tert-butylmethylphorsphonium tetraphenylborate and cesium carbonate, in a solvent, allowing the reaction to be carried out sufficiently at 190° C., and then performing washing, drying and purification to obtain the compound represented by formula (VIII);

step M5: dissolving the compound represented by formula (VIII), along with sodium hydroxide and isopropanol, in a solvent, allowing the reaction to be carried out sufficiently at 40° C. under reflux, and then performing suction filtration and drying, to obtain 13,13-dimethyl-7,13-dihydro-5H-indoloacridine.

The process for preparing the compound represented by formula (I) may comprise producing the compound represented by formula (IV) by reacting R—B(OH)$_2$ with the compound represented by formula (IX):

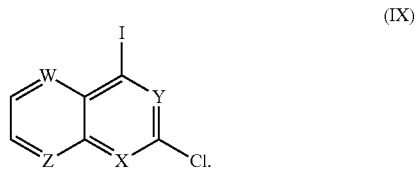

(IX)

Preferably, the compound represented by formula (IV) is obtained by the following Steps N1 to N3:

Step N1: adding the compound represented by formula (IX), R—B(OH)$_2$, potassium carbonate and a solvent into a degassed reaction container;

Step N2: refluxing, allowing the reaction to be carried out sufficiently;

Step N3: obtaining the compound represented by formula (IV) by performing extraction, washing, drying and purification with column chromatography. This compound can be directly used for producing the compound represented by formula (I).

More specifically, the compound represented by formula (IX) and a boric acid having an R substituent are dissolved in toluene. Tetrakis(triphenylphosphine)palladium, potassium carbonate and distilled water are added therein under nitrogen protection. The mixture is stirred under reflux to perform reaction. After the reaction has been completed, the quinazoline having an R substituent is obtained by performing extraction, drying, filtration, distillation under reduced pressure and column chromatography.

For example, some indoloacridine-containing derivatives are produced by the following process: reacting 2-chloro-4-iodoquinazoline with a boric acid having an R substituent to produce a chloride of quinazoline having an R substituent; further reacting the chloride of quinazoline having an R substituent with 13,13-dimethyl-7,13-dihydro-5H-indoloacridine to obtain an indoloacridine-containing derivative. The specific synthesis route is as follows:

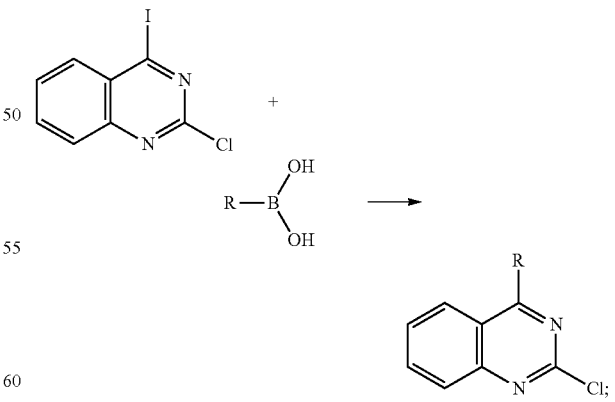

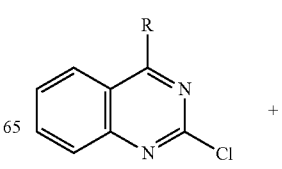

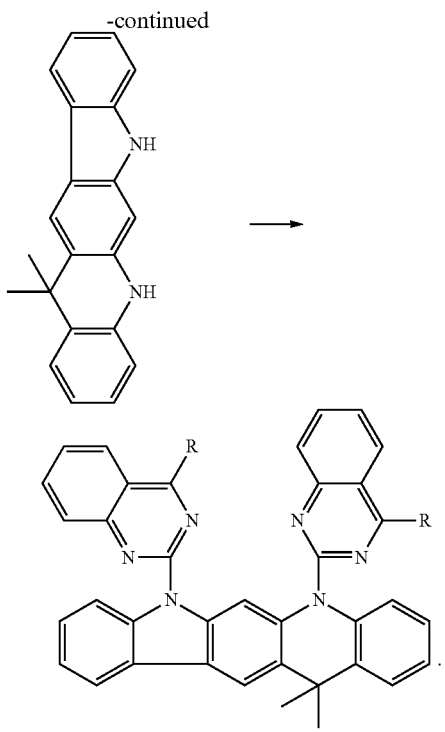

Similar to the above process, the indoloacridine-containing derivatives of the present disclosure can be obtained, by using various compounds represented by formula (IX) to replace 2-chloro-4-iodoquinazoline in the above route.

The present disclosure is described in more detail by the following examples. However, the following examples are only to illustrate the present disclosure more specifically, and the scope of the present disclosure is not limited to the examples. According to the user, the following examples may be modified and changed within the scope of the present disclosure.

Preparation example A: synthesis of the compound represented by formula (III), i.e. 13,13-dimethyl-7,13-dihydro-5H-indoloacridine The process for synthesizing 13,13-dimethyl-7,13-dihydro-5H-indoloacridine is as follows.

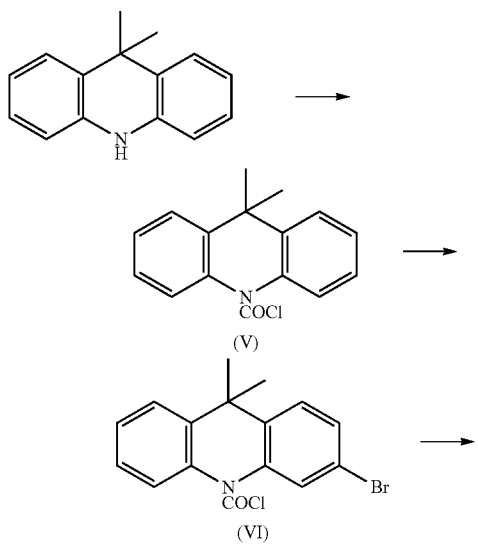

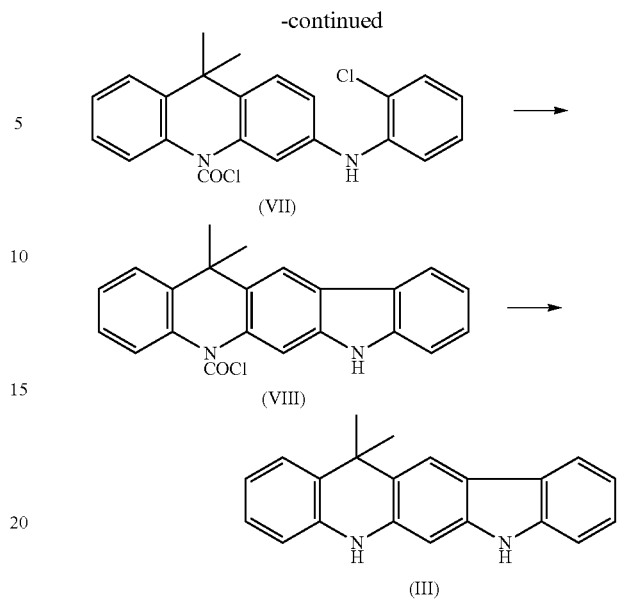

Into a 250 ml three-necked flask equipped with a reflux device, 62.78 g (0.30 mol) of the compound represented by formula (IV), 35.6 g (0.12 mol) of solid triphosgene and 500 ml of toluene were charged. The temperature was raised to a reflux temperature. The reaction was carried out under reflux for 10 h. The end point of the reaction was determined by thin-layer chromatography (TLC). After the reaction was ended, the reaction product was cooled to room temperature, filtered by suction and then dried to obtain 61 g of a pale blue solid. The filtrate was concentrated until it was almost dry. 10 ml of petroleum ether were added thereto. Then filtering by suction and drying were performed, so as to obtain 45.81 g of the compound represented by formula (V), which is a dimethylacridine compound protected by chloroformyl, with a yield of 93.0%.

45.81 g (0.279 mol) of the compound represented by formula (V) were dissolved in 800 ml of DMF (N,N-dimethyl formamide) and stirred at 0° C. for 10 min. A solution of 49.82 g (0.279 mol) of NBS (N-bromosuccinimide) in 350 ml DMF was added thereto slowly. The mixture was stirred at 0° C. for 6 hours. After the reaction was ended, distilled water and ethyl acetate were added into the mixture. The organic layer was dried over anhydrous $MgSO_4$. The solvent was removed by a rotation evaporator. Then, a column chromatography was performed using ethyl acetate to obtain 82.17 g of the compound of formula (VI), which is a dimethylacridine bromide protected by chloroformyl, with a yield of 84%.

82.17 g (0.234 mol) of the compound of formula (VI), 36.28 g (0.281 mol) of 2-chloroaniline, 1.60 g (7.08 mmol) of palladium acetate, 15.55 ml (0.023 mol) of 50% tri-tert-butylphosphine and 154.22 g (0.47 mol) of cesium carbonate were dissolved in 800 ml of toluene. The reaction was performed by stirring at 120° C. for 4 hours. After the reaction was ended, distilled water and ethyl acetate were added into the mixture. The organic layer was dried over anhydrous $MgSO_4$. The solvent was removed by a rotation evaporator. Then, a column chromatography was performed by using ethyl acetate, so as to obtain 72.51 g of the compound of formula (VII), which is a chlorophenyl dimethylacridineamine compound protected by chloroformyl, with a yield of 78%.

72.51 g (0.182 mol) of the compound of formula (VII), 8.34 mg (0.037 mol) of palladium acetate, 18.25 g (0.075 mmol) of di-tert-butyl methylphosphonium tetraphenylborate and cesium carbonate (304.2 g, 0.912 mol) were dissolved in 800 ml of dimethyl acetamide under stirring, and reacted at 190° C. for 4 hours. After the reaction was ended, the mixture was added into distilled water and ethyl acetate. The organic layer was dried over anhydrous MgSO₄. The solvent was removed by a rotation evaporator. Then, a column chromatography was performed by using ethyl acetate, to obtain 53.19 g of the compound of formula (VIII), which is a dimethylacridinoindole compound protected by chloroformyl, with a yield of 81%.

53.19 g (0.147 mol) of the compound of formula (VIII), 17.64 g (0.44 mol) of sodium hydroxide and 300 ml of isopropanol were charged into a 500 ml four-necked flask equipped with a reflux device. The reaction was performed at 40° C. for 3 h. The end point of the reaction was determined by TLC. After the reaction was ended, about 200 ml isopropanol was distilled off under reduced pressure. The pH was adjusted to 12 using a saturated sodium bicarbonate solution. A large amount of solid precipitated. The mixture was stirred for 30 min, followed by suction filtration. The filter cake was washed with 100 ml water. After drying, the yellow compound of formula (III) was obtained, with a yield of 98.2%.

Preparation Example 1: Synthesis of Compound 1

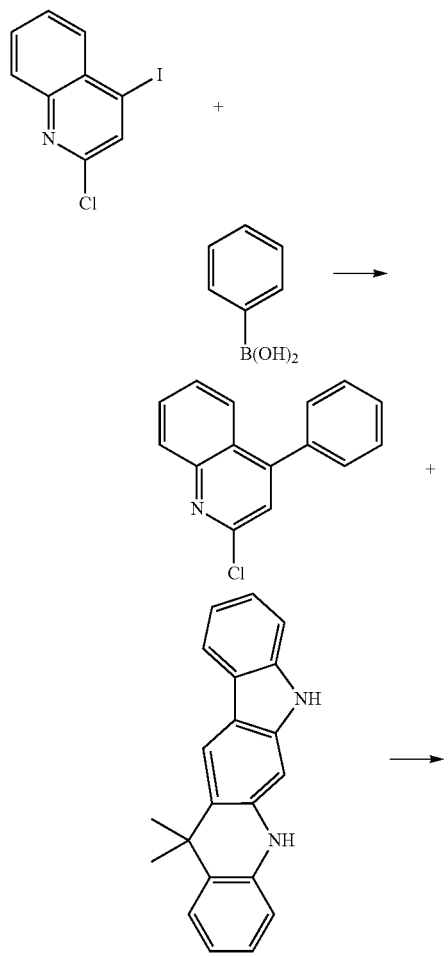

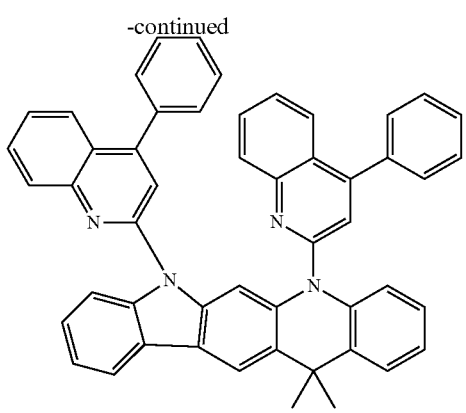
-continued 0.10 mol of 2-chloro-4-iodoquinoline and 0.13 mol of phenyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.072 mol of a white solid intermediate 2-chloro-4-(2-phenyl)quinoline was obtained, with a yield of 72%.

In nitrogen gas, 0.048 mol of the intermediate 2-chloro-4-(2-phenyl)quinoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.036 mol of compound 1, with a yield of 75%.

Preparation Example 2: Synthesis of Compound 2

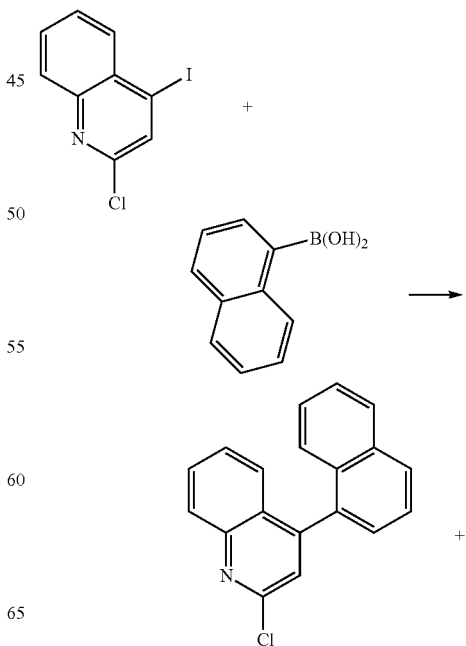

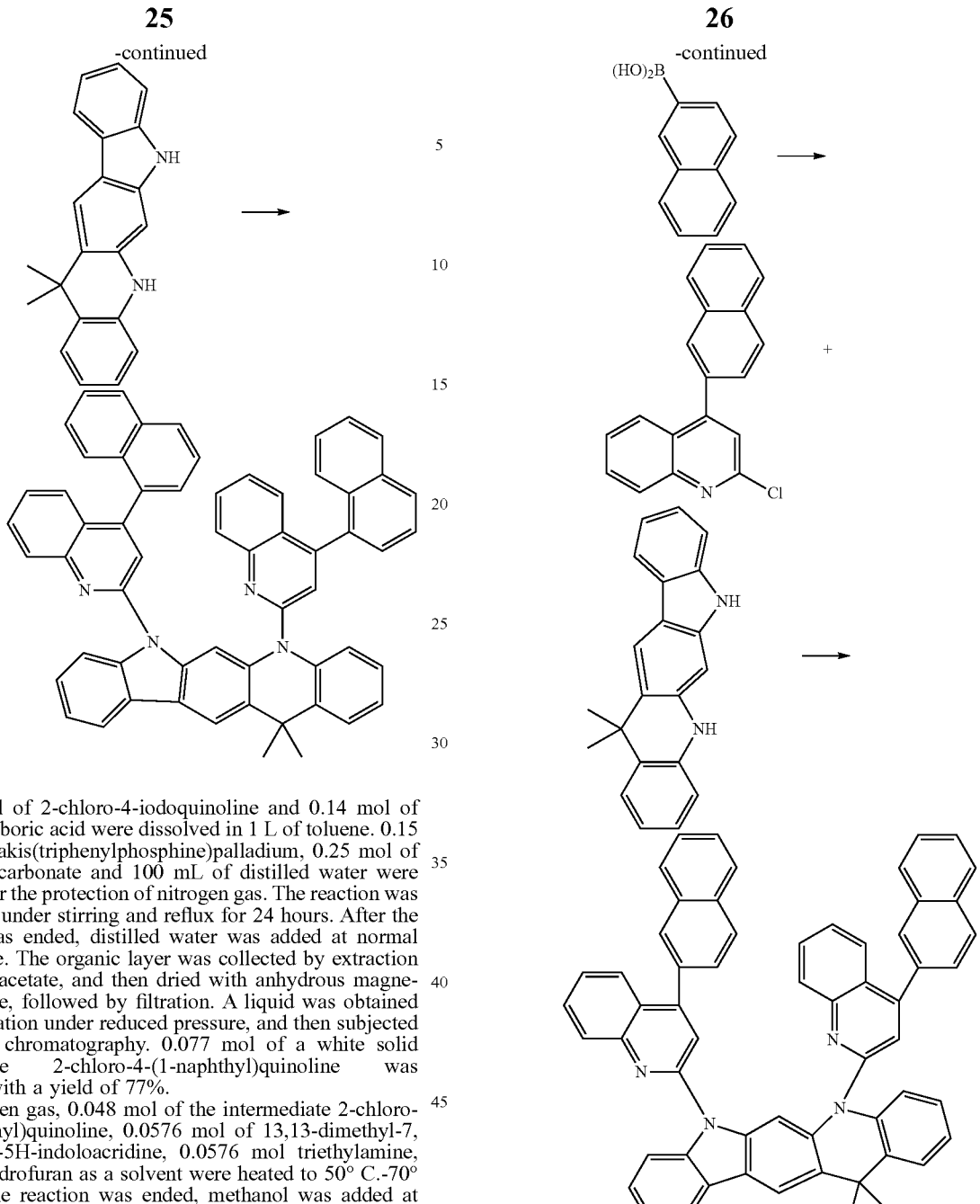

0.10 mol of 2-chloro-4-iodoquinoline and 0.14 mol of 1-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.077 mol of a white solid intermediate 2-chloro-4-(1-naphthyl)quinoline was obtained, with a yield of 77%.

In nitrogen gas, 0.048 mol of the intermediate 2-chloro-4-(1-naphthyl)quinoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0384 mol of compound 2, with a yield of 80%.

Preparation Example 3: Synthesis of Compound 3

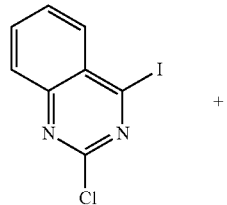

0.10 mol of 2-chloro-4-iodoquinoline and 0.12 mol of 2-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.074 mol of a white solid intermediate 2-chloro-4-(2-naphthyl)quinoline was obtained, with a yield of 74%.

In nitrogen gas, 0.048 mol of the intermediate 2-chloro-4-(2-naphthyl)quinoline, 0.0576 mol of 13,13-dimethyl-7, 13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0379 mol of compound 3, with a yield of 79%.

Preparation Example 4: Synthesis of Compound 4

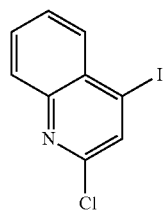

+

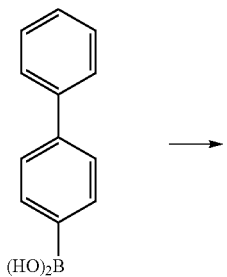

+

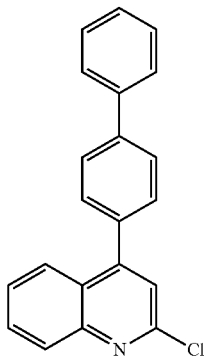

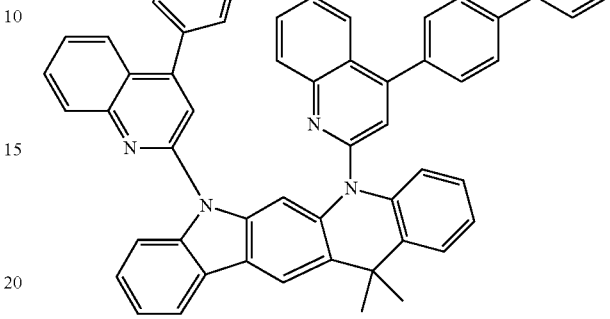

0.10 mol of 2-chloro-4-iodoquinoline and 0.13 mol of 4-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.081 mol of a white solid intermediate 4-([1,1'-biphenyl]-4-yl)-2-chloroquinoline was obtained, with a yield of 81%.

In nitrogen gas, 0.048 mol of the intermediate 4-([1,1'-biphenyl]-4-yl)-2-chloroquinoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0341 mol of compound 4, with a yield of 71%.

Preparation Example 5: Synthesis of Compound 5

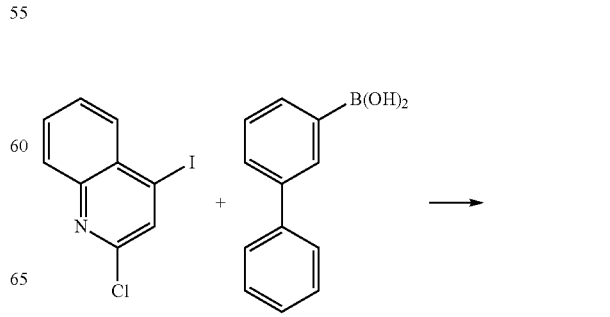

-continued

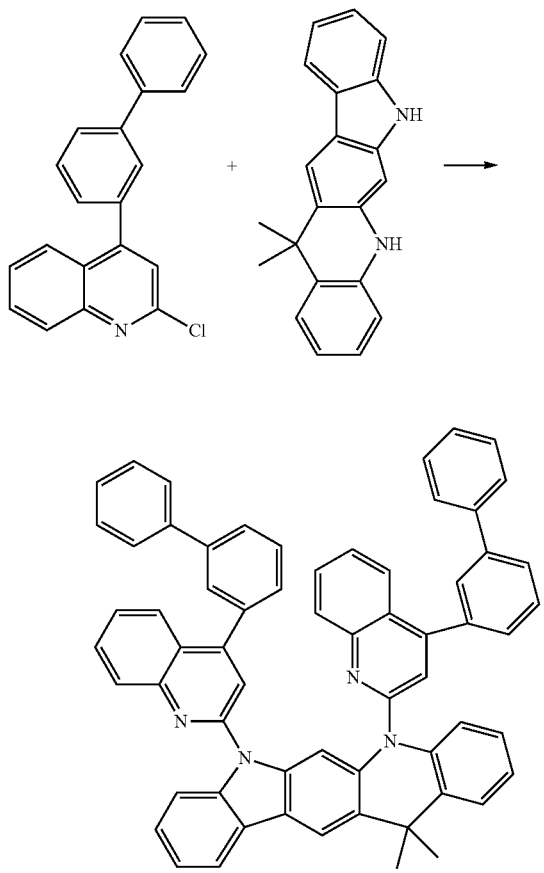

0.10 mol of 2-chloro-4-iodoquinazoline and 0.14 mol of 3-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.078 mol of a white solid intermediate 4-([1,1'-biphenyl]-3-yl)-2-chloroquinoline was obtained, with a yield of 78%.

In nitrogen gas, 0.048 mol of the intermediate 4-([1,1'-biphenyl]-3-yl)-2-chloroquinoline, 0.0576 mol of 13,13-dimethyl-7,13-dihydro-5H-indoloacridine, 0.0576 mol trietylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0369 mol of compound 5, with a yield of 77%.

Preparation Example 6: Synthesis of Compound 6

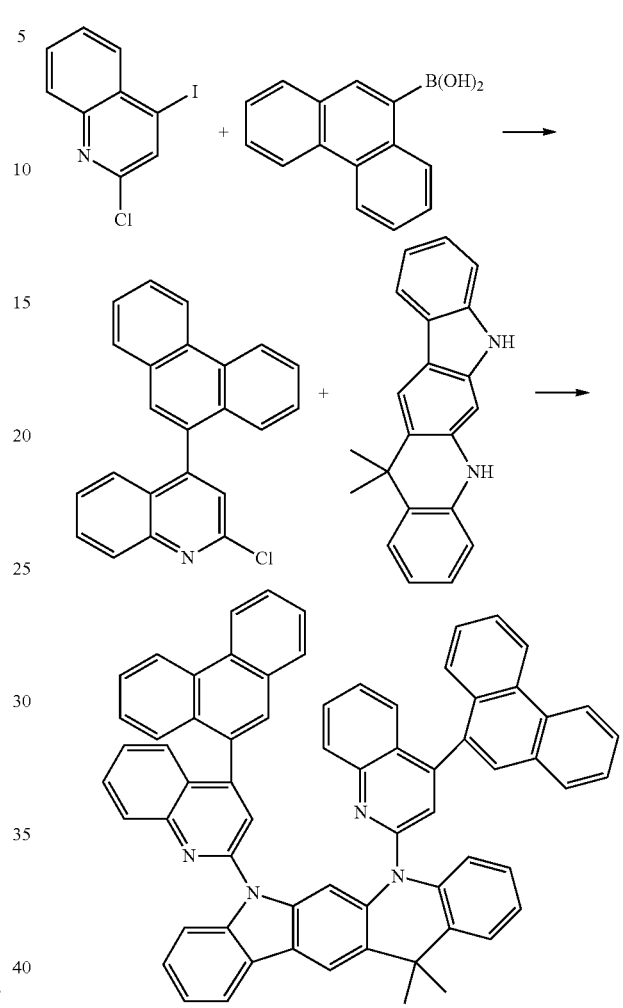

0.10 mol of 2-chloro-4-iodoquinoline and 0.12 mol of 9-phenanthryl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.075 mol of a white solid intermediate 2-chloro-4-(9-phenanthryl)quinoline was obtained, with a yield of 75%.

In nitrogen gas, 0.048 mol of the intermediate 2-chloro-4-(9-phenanthryl)quinoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0389 mol of compound 6, with a yield of 81%.

Preparation Example 7: Synthesis of Compound 7

Example 8: Synthesis of Compound 8

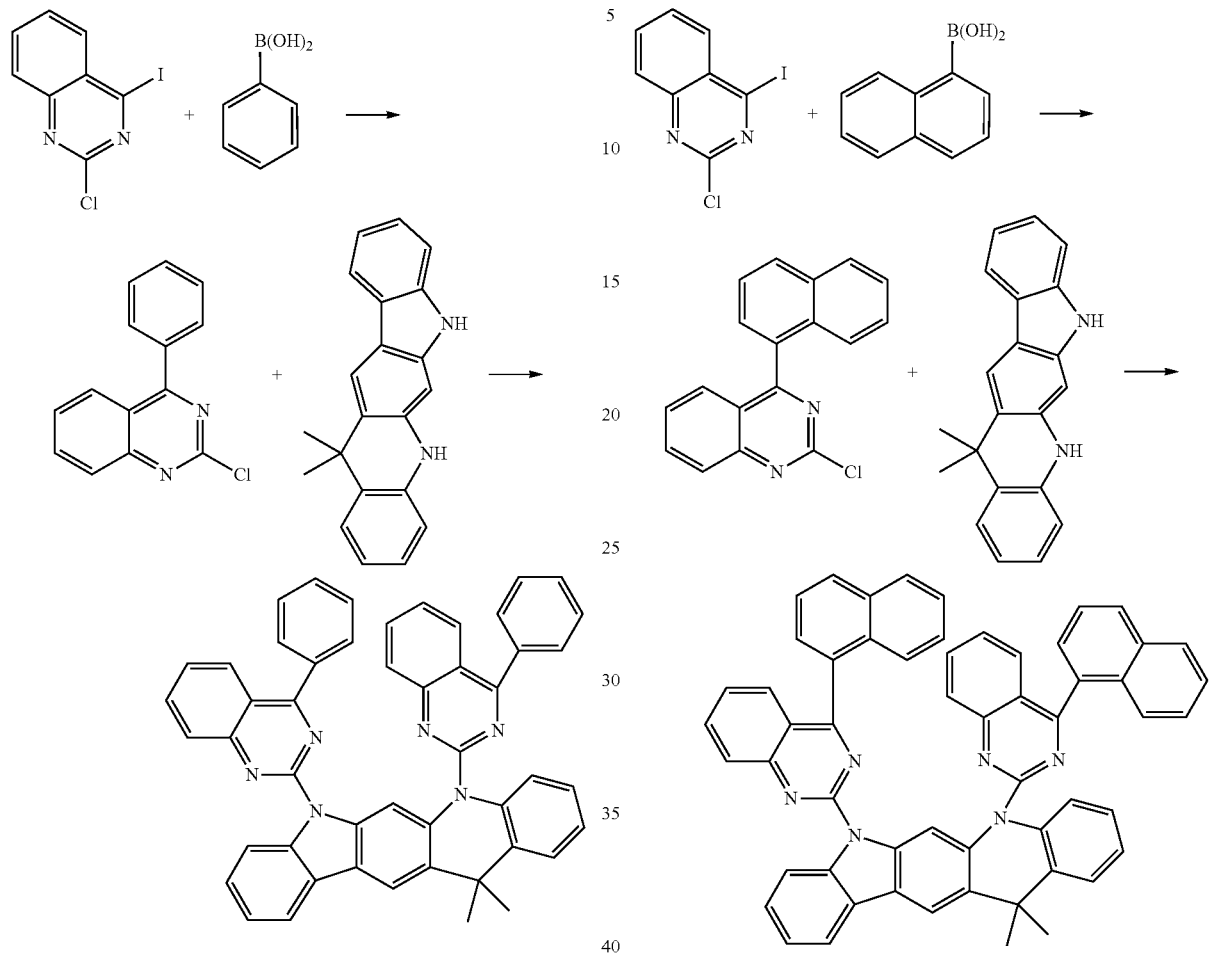

0.10 mol of 2-chloro-4-iodoquinazoline and 0.12 mol of phenyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.082 mol of a white solid intermediate 2-chloro-4-(2-phenyl)quinazoline was obtained, with a yield of 82%.

In nitrogen gas, 0.048 mol of the intermediate 2-chloro-4-(2-phenyl)quinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0384 mol of compound 7, with a yield of 80%.

0.10 mol of 2-chloro-4-iodoquinazoline and 0.13 mol of 1-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.079 mol of a white solid intermediate 2-chloro-4-(2-naphthyl)quinazoline was obtained, with a yield of 79%.

In nitrogen gas, 0.048 mol of the intermediate 2-chloro-4-(1-naphthyl)quinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0350 mol of compound 8, with a yield of 73%.

Preparation Example 9: Synthesis of Compound 9

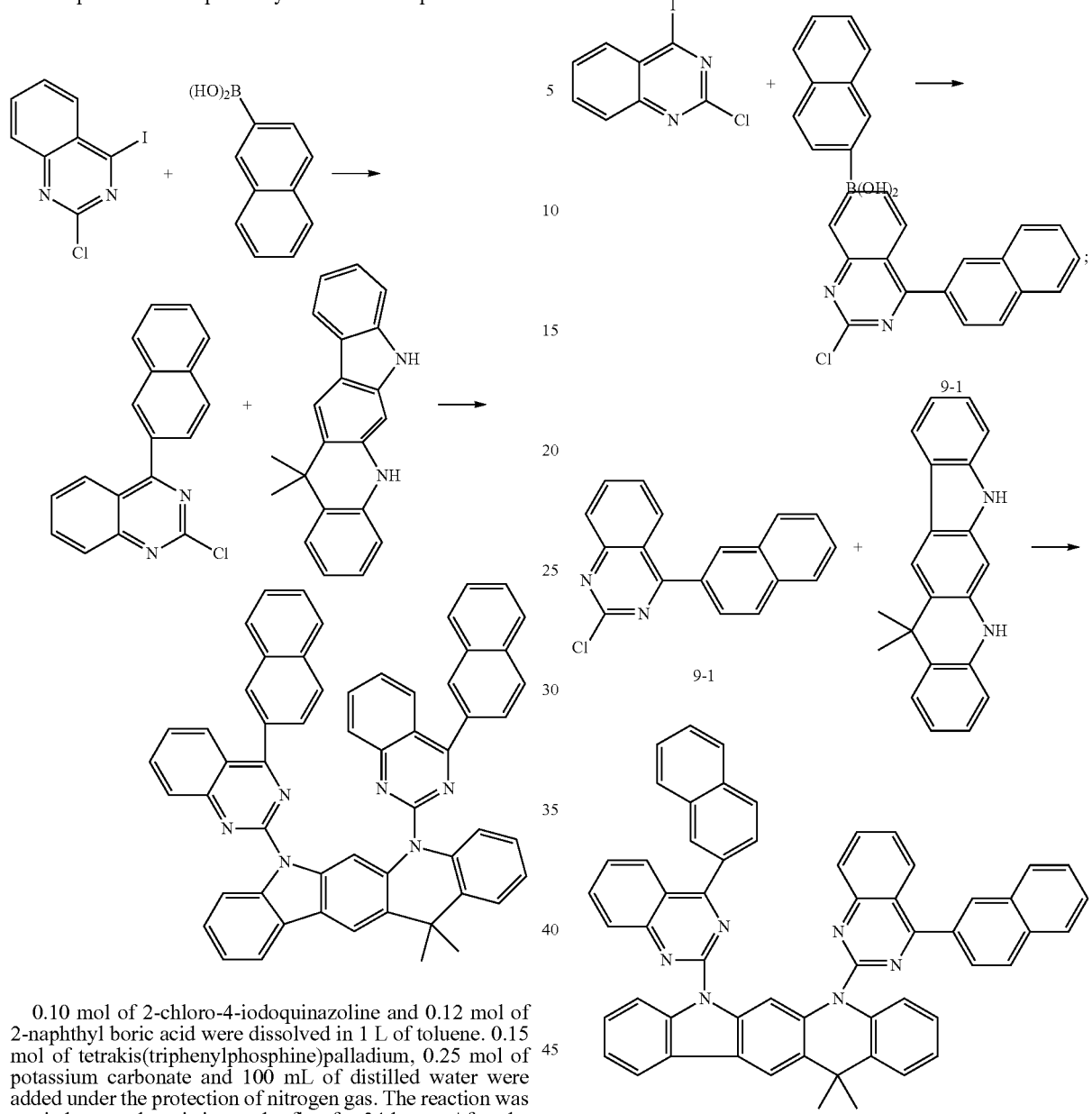

0.10 mol of 2-chloro-4-iodoquinazoline and 0.12 mol of 2-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-(2-naphthyl)quinazoline was obtained, with a yield of 76%.

In nitrogen gas, 0.048 mol of the intermediate 2-chloro-4-(2-naphthyl)quinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0384 mol of compound 9, with a yield of 80%.

The compound 9 also can be synthesized by following process. This process was applicable for synthesizing compounds 1-8 and 10-24, too.

Synthesis of Intermediate Compound 9-1

29.05 g (0.1 mol) of 2-chloro-4-iodoquinazoline and 20.64 g (0.12 mmol) of 2-naphthyl boric acid were dissolved in 1 L of toluene. 11.7 g (10.15 mol) of tetrakis(triphenylphosphine)palladium, 34.55 g (0.25 mol) of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 22.1 g of a white solid intermediate compound 9-1 was obtained, with a yield of 76%.

Synthesis of Compound 9

In nitrogen gas, 13.96 g (0.048 mol) of the intermediate 9-1, 5.97 g (0.02 mol) of 13,13-dimethyl-7,13-dihydro-5H- indoloacridine, 1.52 g (0.008 mol) of copper iodide, 3.09 g (0.055 mol) of potassium hydroxide, 1.16 g of (0.008 mol) 8-hydroxyquinoline and 100 ml of dimethyl sulfoxide (DMSO) were heated to 150° C. and stirred. After the reaction was ended, methanol was added at normal temperature, and then the produced solid was filtered off. The solid filtered off was added into and washed with distilled water and methanol. Then recrystallization was performed with dichloromethane and methanol, so as to obtain 12.91 g of compound 9, with a yield of 80%.

The HPLC purity was higher than 99%. Mass Spectrum: the calculated value was 806.95; the measured value was 806.96. Element Analysis: calculated values are C, 84.84%; H, 4.75%; N, 10.41%; measured values are C, 84.83%; H, 4.76%; N, 10.41%.

Preparation Example 10: Synthesis of Compound 10

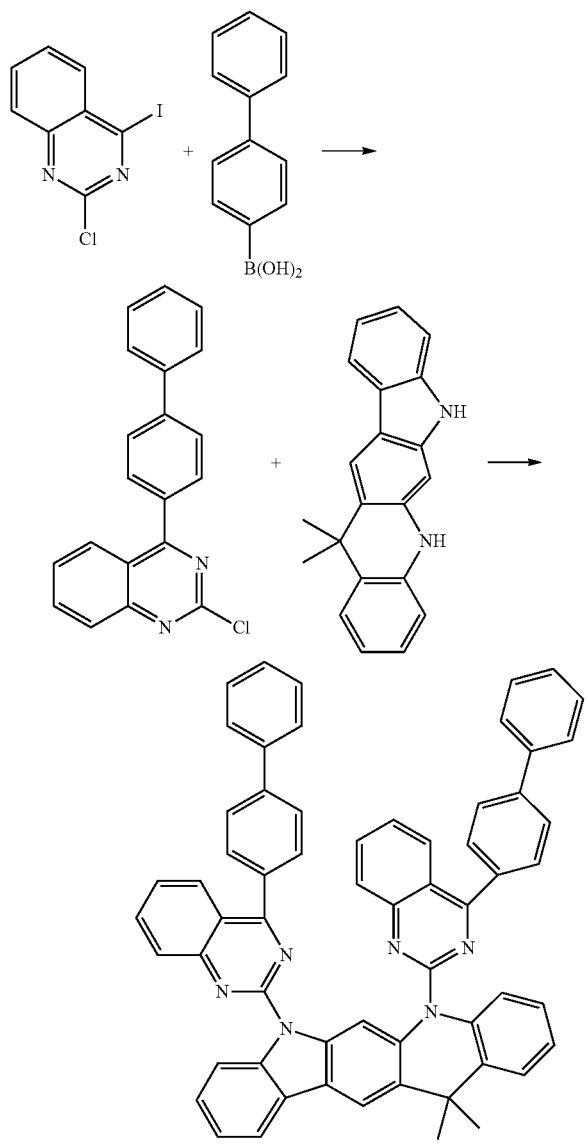

0.10 mol of 2-chloro-4-iodoquinazoline and 0.12 mol of 4-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.073 mol of a white solid intermediate 4-([1,1'-biphenyl]-4-yl)-2-chloroquinazoline was obtained, with a yield of 73%.

In nitrogen gas, 0.048 mol of the intermediate 4-([1,1'-biphenyl]-4-yl)-2-chloroquinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0394 mol of compound 10, with a yield of 82%.

Preparation Example 11: Synthesis of Compound 11

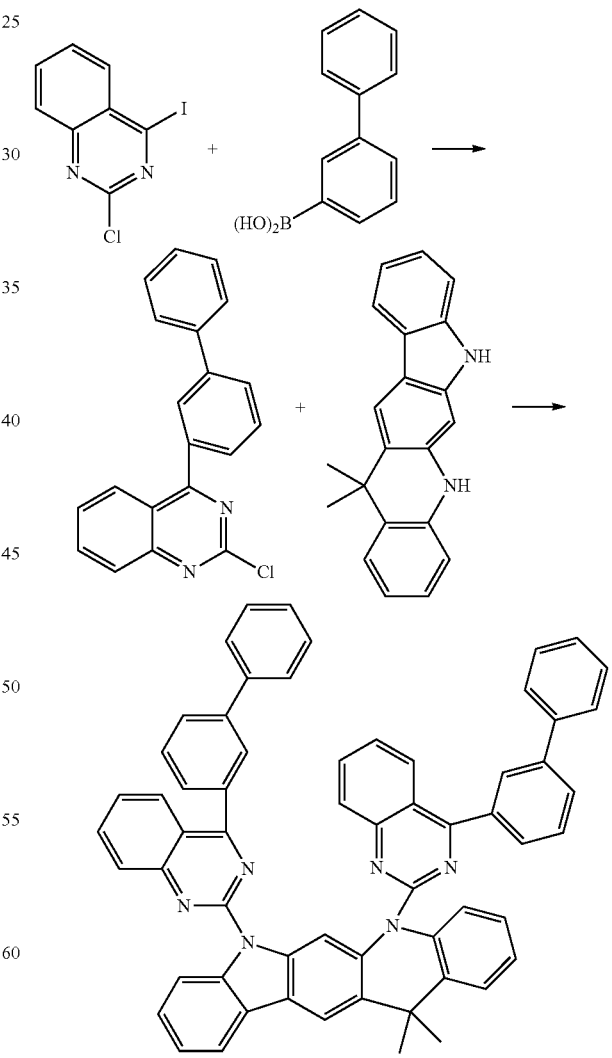

0.10 mol of 2-chloro-4-iodoquinazoline and 0.11 mol of 3-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.078 mol of a white solid intermediate 4-([1,1'-biphenyl]-3-yl)-2-chloroquinazoline was obtained, with a yield of 78%.

In nitrogen gas, 0.048 mol of the intermediate 4-([1,1'-biphenyl]-3-yl)-2-chloroquinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0355 mol of compound 11, with a yield of 74%.

Preparation Example 12: Synthesis of Compound 12

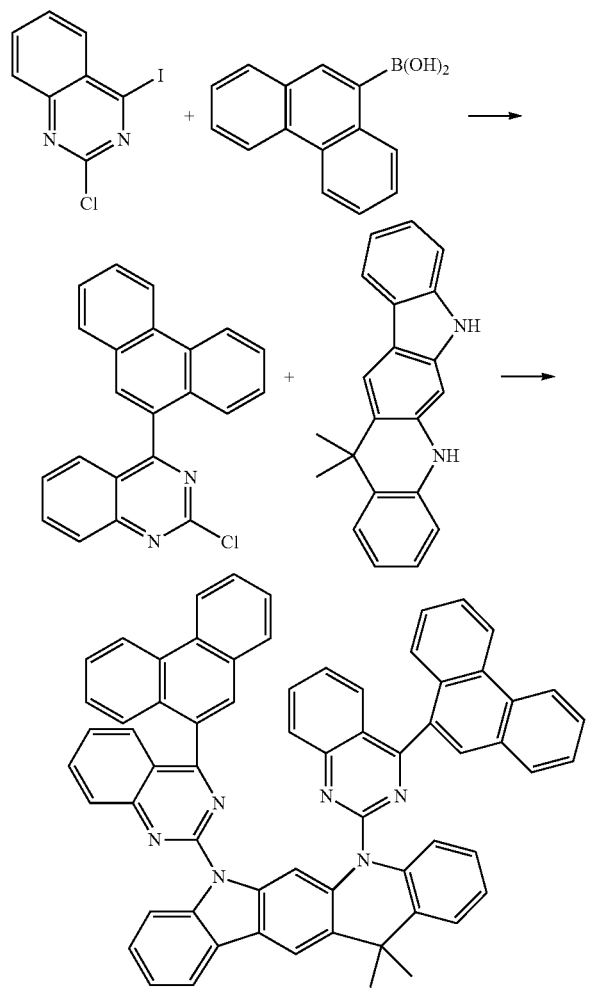

0.10 mol of 2-chloro-4-iodoquinazoline and 0.12 mol 9-phenanthryl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.073 mol of a white solid intermediate 2-chloro-4-(9-phenanthryl)quinazoline was obtained, with a yield of 73%.

In nitrogen gas, 0.048 mol of the intermediate 2-chloro-4-(9-phenanthryl)quinazoline, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0340 mol of compound 12, with a yield of 71%.

Preparation Example 13: Synthesis of Compound 13

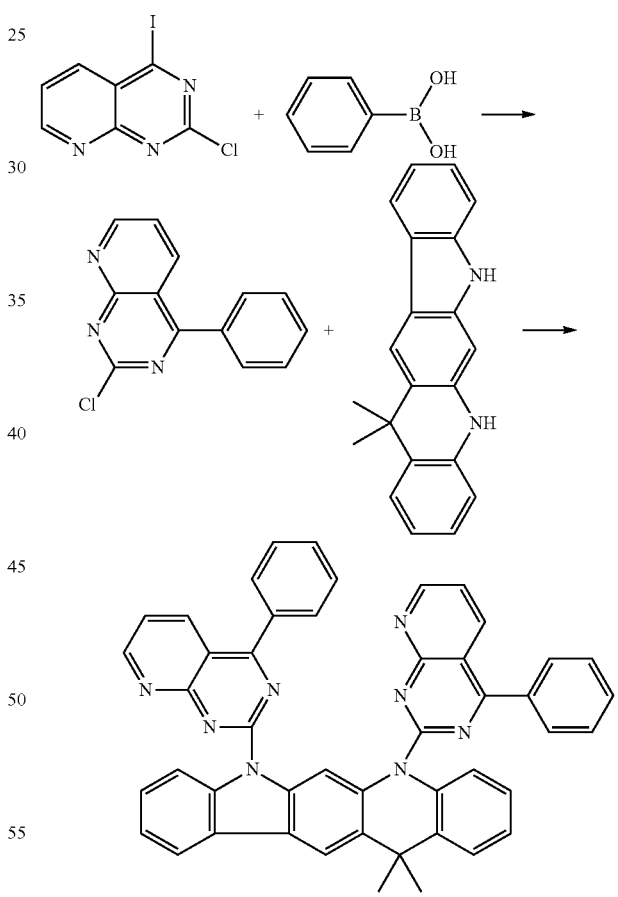

0.10 mol of 2-chloro-4-iodopyrido[2,3-d]pyrimidine and 0.13 mol of phenyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.074 mol of a white solid intermediate 2-chloro-4-phenylpyrido[2,3-d]pyrimidine was obtained, with a yield of 74%.

In nitrogen gas, 0.0480 mol of the intermediate 2-chloro-4-phenylpyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0374 mol of compound 13, with a yield of 78%.

Preparation Example 14: Synthesis of Compound 14

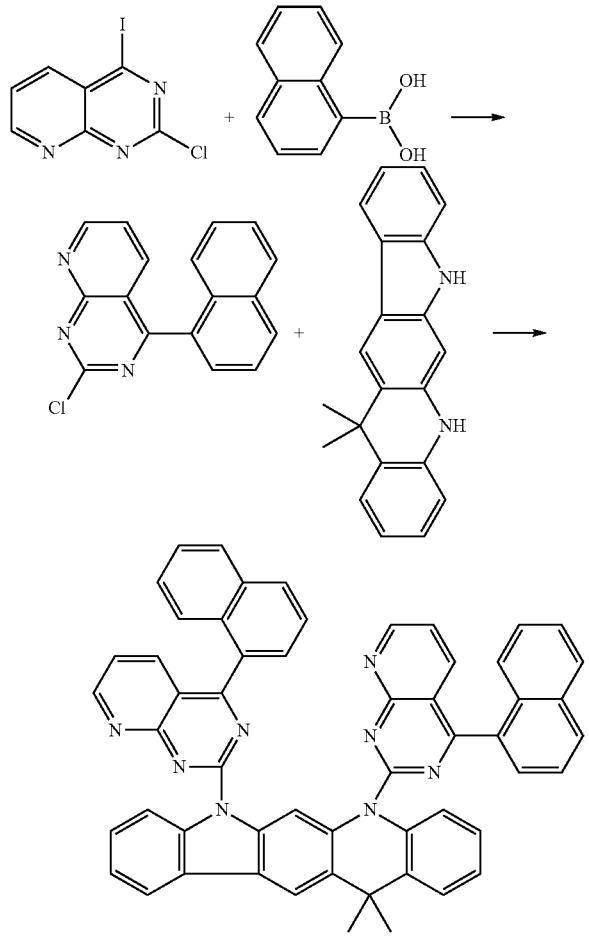

0.10 mol of 2-chloro-4-iodopyrido[2,3-d]pyrimidine and 0.12 mol of 1-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-(1-naphthyl)pyrido[2,3-d]pyrimidine was obtained, with a yield of 76%.

In nitrogen gas, 0.048 mol of the intermediate 2-chloro-4-(1-naphthyl)pyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0370 mol of compound 14, with a yield of 77%.

Preparation Example 15: Synthesis of Compound 15

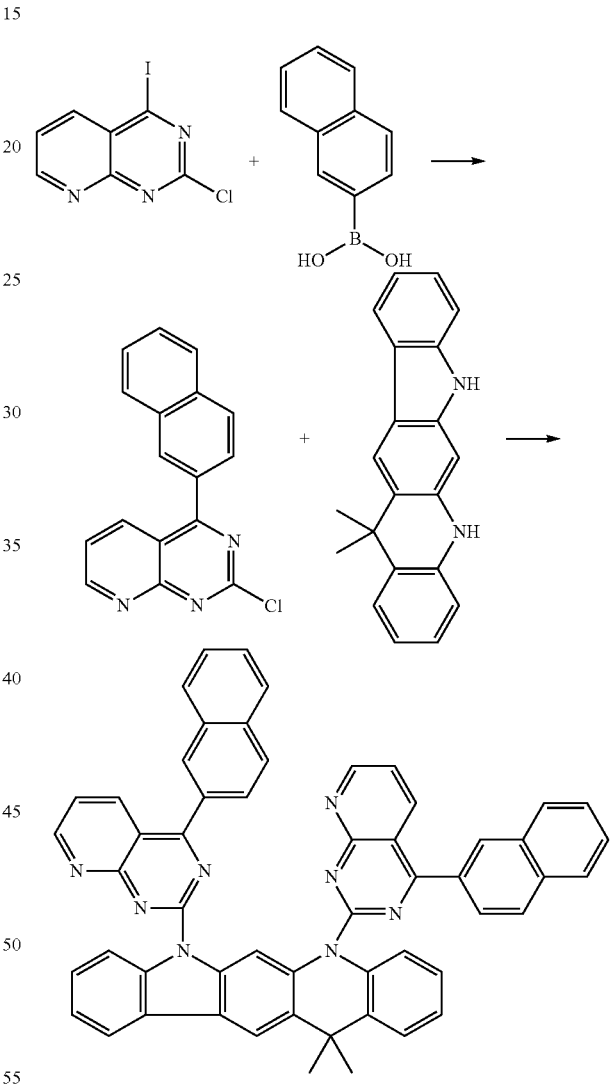

0.10 mol of 2-chloro-4-iodopyrido[2,3-d]pyrimidine and 0.12 mol of 2-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-(2-naphthyl)pyrido[2,3-d]pyrimidine was obtained, with a yield of 76%.

In nitrogen gas, 0.048 mol of the intermediate 2-chloro-4-(2-naphthyl)pyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0370 mol of compound 15, with a yield of 77%.

Preparation Example 16: Synthesis of Compound 16

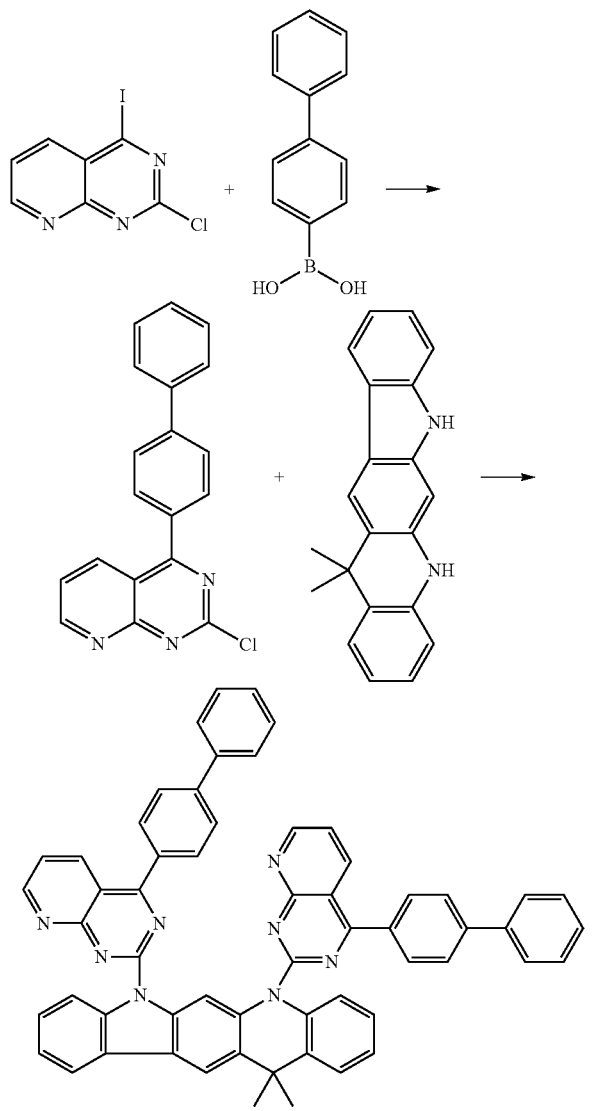

0.10 mol of 2-chloro-4-iodopyrido[2,3-d]pyrimidine and 0.12 mol of 4-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.0740 mol of a white solid intermediate 4-([1,1'-biphenyl]-4-yl)-2-chloropyrido[2,3-d]pyrimidine was obtained, with a yield of 74%.

In nitrogen gas, 0.048 mol of the intermediate 4-([1,1'-biphenyl]-4-yl)-2-chloropyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0374 mol of compound 16, with a yield of 78%.

Preparation Example 17: Synthesis of Compound 17

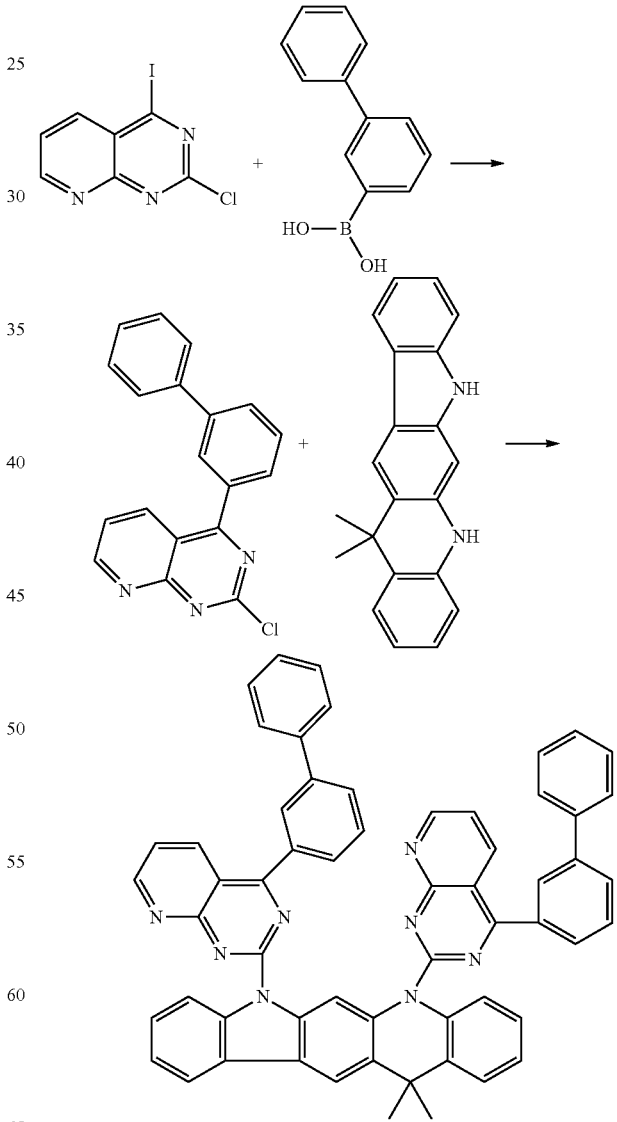

0.10 mol of 2-chloro-4-iodopyrido[2,3-d]pyrimidine and 0.14 mol of 3-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.0780 mol of a white solid intermediate 4-([1,1'-biphenyl]-3-yl)-2-chloropyrido[2,3-d]pyrimidine was obtained, with a yield of 78%.

In nitrogen gas, 0.048 mol of the intermediate 4-([1,1'-biphenyl]-3-yl)-2-chloropyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0379 mol of compound 17, with a yield of 79%.

Preparation Example 18: Synthesis of Compound 18

0.10 mol of 2-chloro-4-iodopyrido[2,3-d]pyrimidine and 0.12 mol of 9-phenanthryl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-(9-phenanthryl)pyrido[2,3-d]pyrimidine was obtained, with a yield of 76%.

In nitrogen gas, 0.048 mol of the intermediate 2-chloro-4-(9-phenanthryl)pyrido[2,3-d]pyrimidine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0374 mol of compound 18, with a yield of 78%.

Preparation Example 19: Synthesis of Compound 19

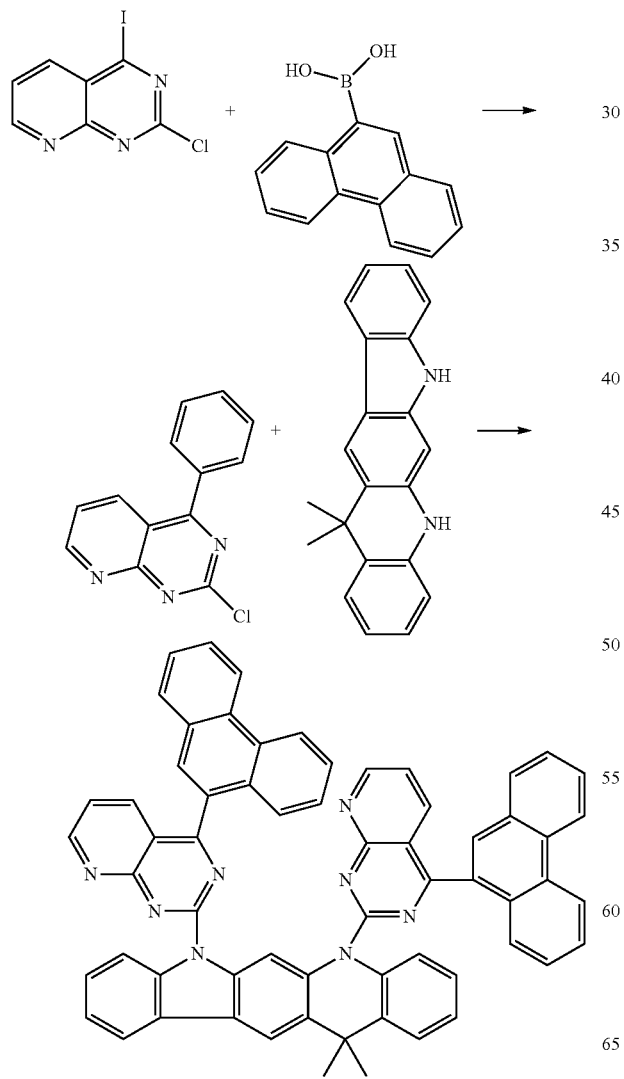

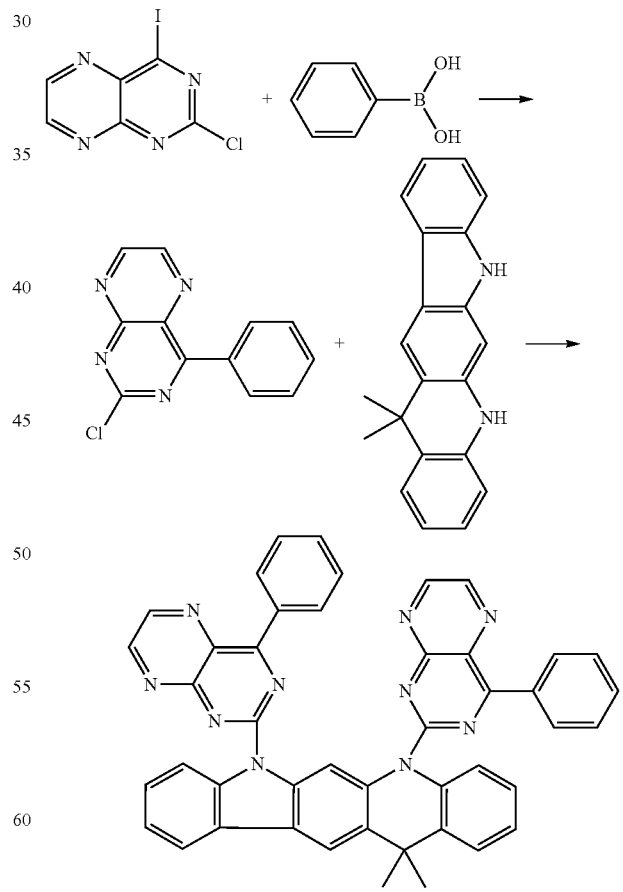

0.10 mol of 2-chloro-4-iodopteridine and 0.13 mol of phenyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-phenylpteridine was obtained, with a yield of 76%.

In nitrogen gas, 0.048 mol of the intermediate 2-chloro-4-phenylpteridine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0374 mol of compound 19, with a yield of 78%.

temperature. The organic layer was collected by extraction with ethyl acetate, and then dried with anhydrous magnesium sulfate, followed by filtration. A liquid was obtained after distillation under reduced pressure, and then subjected to column chromatography. 0.074 mol of a white solid intermediate 2-chloro-4-(1-naphthyl)pteridine was obtained, with a yield of 74%.

In nitrogen gas, 0.048 mol of the intermediate 2-chloro-4-(1-naphthyl)pteridine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0365 mol of compound 20, with a yield of 76%.

Preparation Example 20: Synthesis of Compound 20

Preparation Example 21: Synthesis of Compound 21

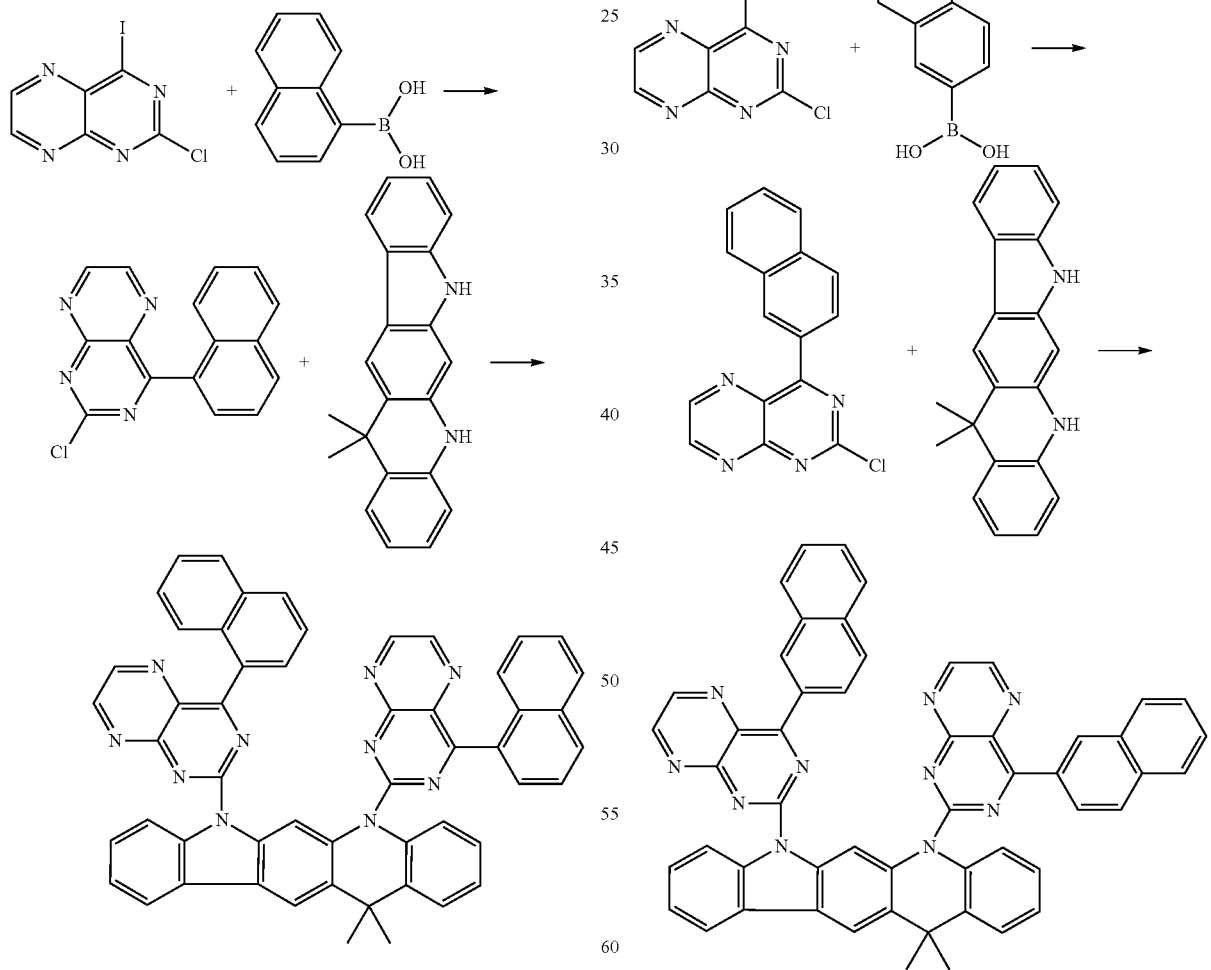

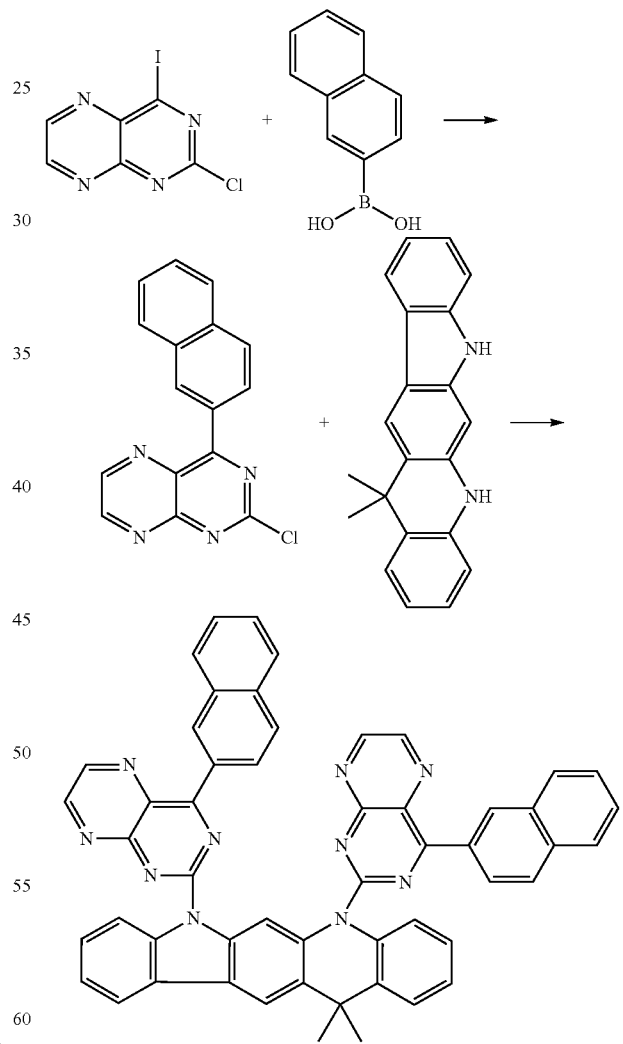

0.10 mol of 2-chloro-4-iodopteridine and 0.14 mol of 1-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal 0.10 mol of 2-chloro-4-iodopteridine and 0.13 mol of 2-naphthyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.074 mol of a white solid intermediate 2-chloro-4-(2-naphthyl)pteridine was obtained, with a yield of 74%.

In nitrogen gas, the intermediate 2-chloro-4-(2-naphthyl) pteridine 0.048 mol, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0360 mol of compound 21, with a yield of 75%.

Preparation Example 22: Synthesis of Compound 22 were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.074 mol of a white solid intermediate 4-([1,1'-biphenyl]-4-yl)-2-pteridine was obtained, with a yield of 74%.

In nitrogen gas, 0.048 mol of the intermediate 4-([1,1'-biphenyl]-4-yl)-2-pteridine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.03552 mol of compound 22, with a yield of 74%.

Preparation Example 23: Synthesis of Compound 23

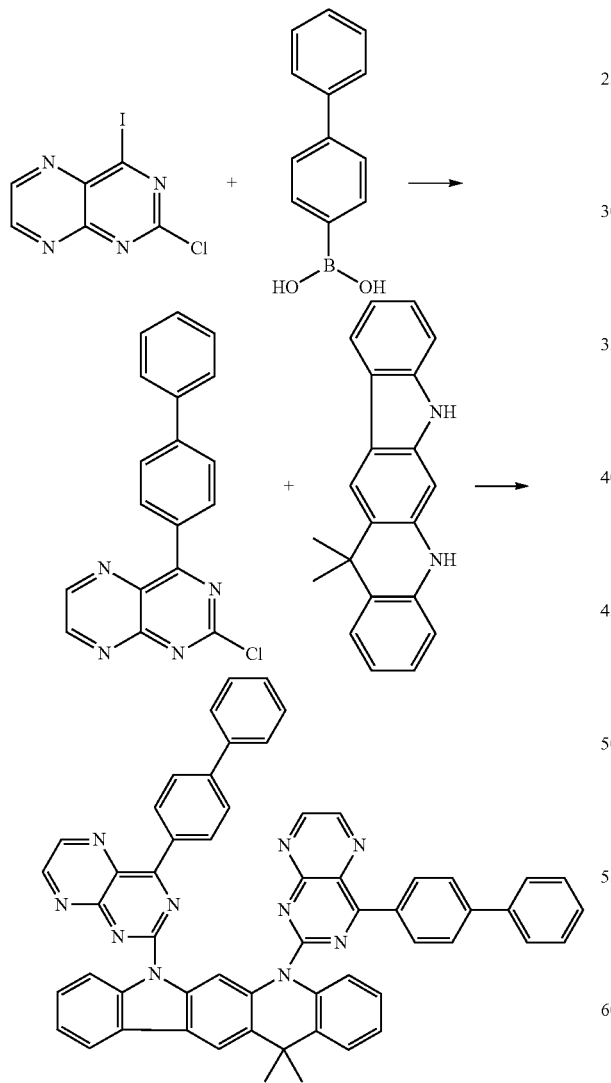

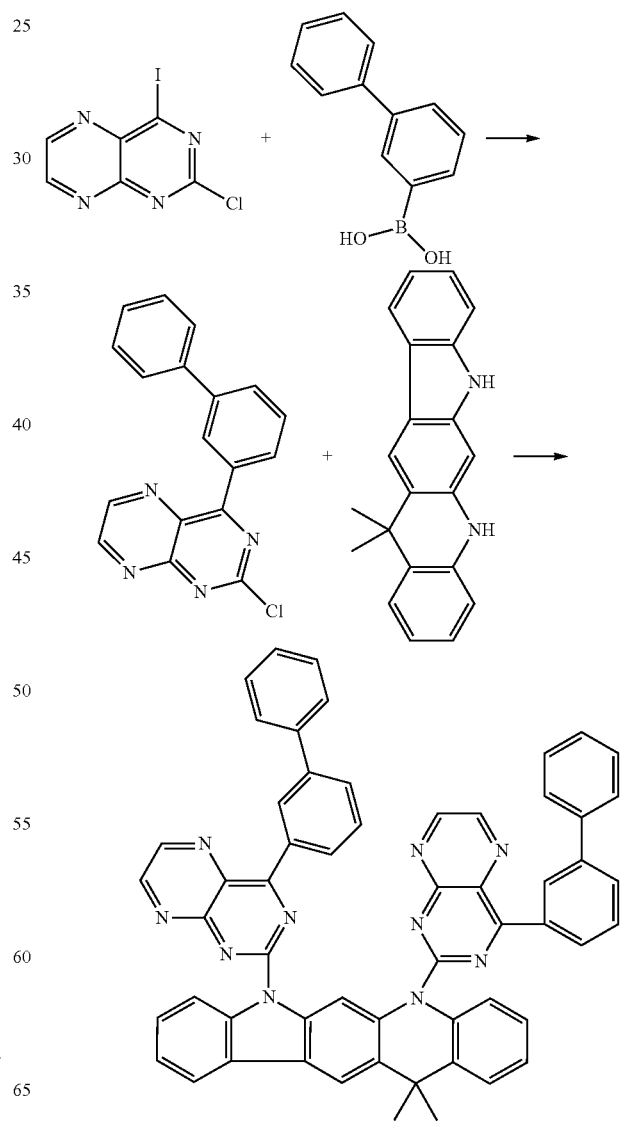

0.10 mol of 2-chloro-4-iodopteridine and 0.14 mol of 4-biphenylyl boric acid were dissolved in 1 L of toluene. 0.15 mol of tetrakis(triphenylphosphine)palladium, 0.25 mol of potassium carbonate and 100 mL of distilled water 0.10 mol of 2-chloro-4-iodopteridine and 0.12 mol 3-biphenylyl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 4-([1,1'-biphenyl]-3-yl)-2-pteridine was obtained, with a yield of 76%.

In nitrogen gas, 0.048 mol of the intermediate 4-([1,1'-biphenyl]-3-yl)-2-pteridine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0365 mol of compound 9, with a yield of 76%.

Example 24: Synthesis of Compound 24

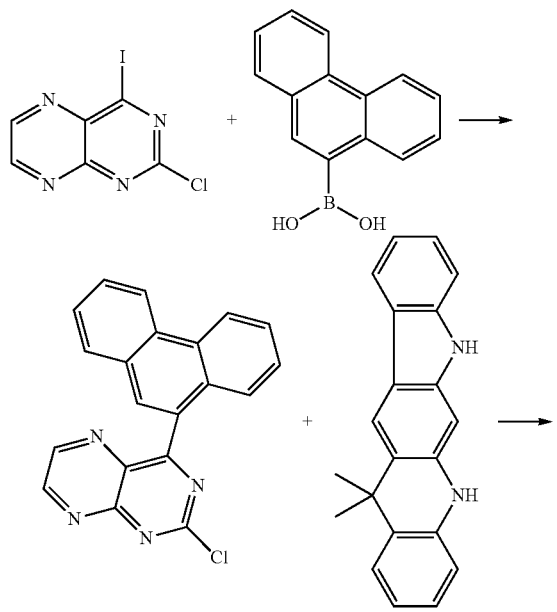

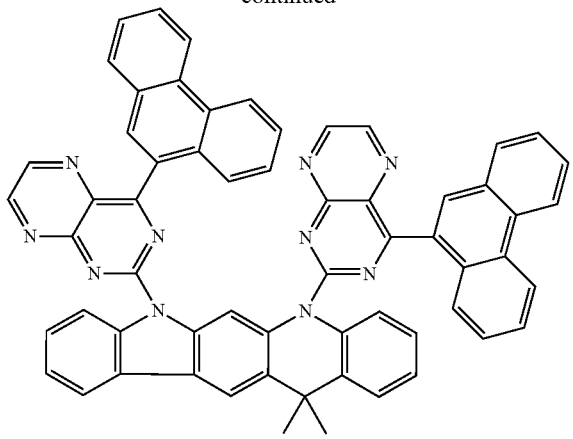

0.10 mol of 2-chloro-4-iodopteridine and 0.14 mol of 9-phenanthryl boric acid were dissolved in 1 L of toluene. 0.15 mol of tetrakis(triphenylphosphine)palladium, 0.25 mol of potassium carbonate and 100 mL of distilled water were added under the protection of nitrogen gas. The reaction was carried out under stirring and reflux for 24 hours. After the reaction was ended, distilled water was added at normal temperature. The organic layer was collected by extraction with ethyl acetate, and then dried with anhydrous magnesium sulfate, followed by filtration. A liquid was obtained after distillation under reduced pressure, and then subjected to column chromatography. 0.076 mol of a white solid intermediate 2-chloro-4-(9-phenanthryl)pteridine was obtained, with a yield of 76%.

In nitrogen gas, 0.048 mol of the intermediate 2-chloro-4-(9-phenanthryl)pteridine, 0.0576 mol of 13,13-dimethyl-7,13-dihydro-5H-indoloacridine, 0.0576 mol triethylamine, and tetrahydrofuran as a solvent were heated to 50° C.-70° C. After the reaction was ended, methanol was added at normal temperature, and then the produced solid was filtered off. The solid filtered off was added into and washed with distilled water and methanol. Then recrystallization was performed with dichloromethane and methanol, so as to obtain 0.0370 mol of compound 24, with a yield of 77%.

Compounds 1-24 were synthesized by the above-mentioned Examples of reaction. The element analysis of the compounds was carried out by fast atom bombardment mass spectroscopy (FABMS) method. The results were listed in Table 2, wherein MS/FAB(M+) was the molecular weight measured by FABMS.

TABLE 2

| Compound No. | Element Analysis | MS/FAB (M+) |
|---|---|---|
| 1 | calculated values are C: 86.90%; H: 5.15%; N: 7.95%; measured values are C: 86.91%; H: 5.15%; N: 7.94%; | 704.86 |
| 2 | calculated values are C: 88.03%; H: 5.01%; N: 6.96%; measured values are C: 88.02%; H: 5.00%; N: 6.98%; | 804.98 |
| 3 | calculated values are C: 88.03%; H: 5.01%; N: 6.96%; measured values are C: 88.05%; H: 5.02%; N: 6.93%; | 804.98 |
| 4 | calculated values are C: 88.29%; H: 5.17%; N: 6.54%; measured values are C: 88.30%; H: 5.18%; N: 6.52%; | 857.05 |
| 5 | calculated values are C: 88.29%; H: 5.17%; N: 6.54%; measured values are C: 88.28%; H: 5.16%; N: 6.56%; | 857.05 |
| 6 | calculated values are C: 88.91%; H: 4.90%; N: 6.19%; measured values are C: 88.90%; H: 4.90%; N: 6.20%; | 905.09 |
| 7 | calculated values are C: 83.26%; H: 4.85%; N: 11.89%; measured values are C: 83.26%; H: 4.86%; N: 11.88%; | 706.83 |

TABLE 2-continued

| Compound No. | Element Analysis | MS/FAB (M+) |
|---|---|---|
| 8 | calculated values are C: 84.84%; H: 4.75%; N: 10.41%; measured values are C: 84.86%; H: 4.76%; N: 10.38%; | 806.95 |
| 9 | calculated values are C: 84.84%; H: 4.75%; N: 10.41%; measured values are C: 84.83%; H: 4.76%; N: 10.41%; | 806.95 |
| 10 | calculated values are C: 85.29%; H: 4.93%; N: 9.78%; measured values are C: 85.29%; H: 4.92%; N: 9.79%; | 859.03 |
| 11 | calculated values are C: 85.29%; H: 4.93%; N: 9.78%; measured values are C: 85.30%; H: 4.93%; N: 9.77%; | 859.03 |
| 12 | calculated values are C: 86.07%; H: 4.67%; N: 9.27%; measured values are C: 86.05%; H: 4.66%; N: 9.30%; | 907.07 |
| 13 | calculated values are C: 79.64%; H: 4.55%; N: 15.81%; measured values are C: 79.66%; H: 4.55%; N: 15.79%; | 708.81 |
| 14 | calculated values are C: 81.66%; H: 4.49%; N: 13.85%; measured values are C: 81.65%; H: 4.50%; N: 13.85%; | 808.93 |
| 15 | calculated values are C: 81.66%; H: 4.49%; N: 13.85%; measured values are C: 81.65%; H: 4.48%; N: 13.87%; | 808.93 |
| 16 | calculated values are C: 82.30%; H: 4.68%; N: 13.01%; measured values are C: 82.30%; H: 4.69%; N: 13.00%; | 861.00 |
| 17 | calculated values are C: 82.30%; H: 4.68%; N: 13.01%; measured values are C: 82.32%; H: 4.68%; N: 12.99%; | 861.00 |
| 18 | calculated values are C: 83.24%; H: 4.44%; N: 12.33%; measured values are C: 83.25%; H: 4.45%; N: 12.31%; | 909.05 |
| 19 | calculated values are C: 76.04%; H: 4.25%; N: 19.71%; measured values are C: 76.05%; H: 4.25%; N: 19.70%; | 710.79 |
| 20 | calculated values are C: 78.50%; H: 4.23%; N: 17.27%; measured values are C: 78.51%; H: 4.24%; N: 17.25%; | 810.90 |
| 21 | calculated values are C: 78.50%; H: 4.23%; N: 17.27%; measured values are C: 78.50%; H: 4.21%; N: 17.29%; | 810.90 |
| 22 | calculated values are C: 79.33%; H: 4.44%; N: 16.23%; measured values are C: 79.32%; H: 4.46%; N: 16.22%; | 862.98 |
| 23 | calculated values are C: 79.33%; H: 4.44%; N: 16.23%; measured values are C: 79.34%; H: 4.44%; N: 16.22%; | 862.98 |
| 24 | calculated values are C: 80.42%; H: 4.20%; N: 15.37%; measured values are C: 80.41%; H: 4.21%; N: 15.37%; | 911.02 |

It can be seen from the above results that the measured results are consistent with the calculated results, indicating that the produced compounds 1 to 24 are exactly the compounds (1) to (24).

Organic electroluminescent devices were prepared by using the compounds 1-24 prepared from the above preparation examples, and then compared with the comparative sample. In the organic electroluminescent devices, the compound of formula (I) can be used as a red phosphorescence host material, a hole-injecting material or a hole-transporting material. The disclosure was illustrated below by using the compound as a red phosphorescence host material.

Comparative Example 1

An organic electroluminescent device having the following structure was prepared by using a compound of chemical formula a as a luminescent host material, a compound of chemical formula b as a doping material, 2-TNATA (4,4,4-tri(N-naphthyl)-N-phenylamino)-triphenylamine) represented by chemical formula c as a hole-injecting material, and α-NPD (N,N'-di(naphthyl)-N,N'-diphenylbenzidine) represented by chemical formula d as a hole-transporting material:

ITO/2-TNATA(80 nm)/α-NPD(30 nm)/compound a+compound b(30 nm, content of b therein being 8%)/Alq$_3$ (30 nm)/LiF(0.5 nm)/Al(60 nm).

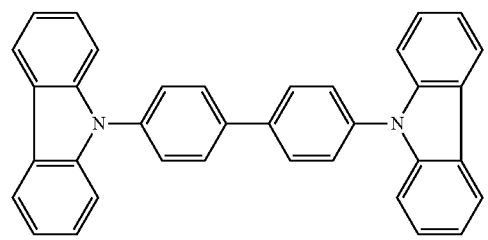

chemical formula a

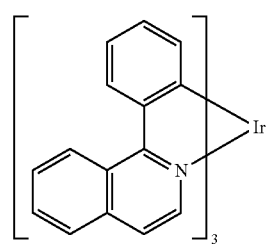

chemical formula b

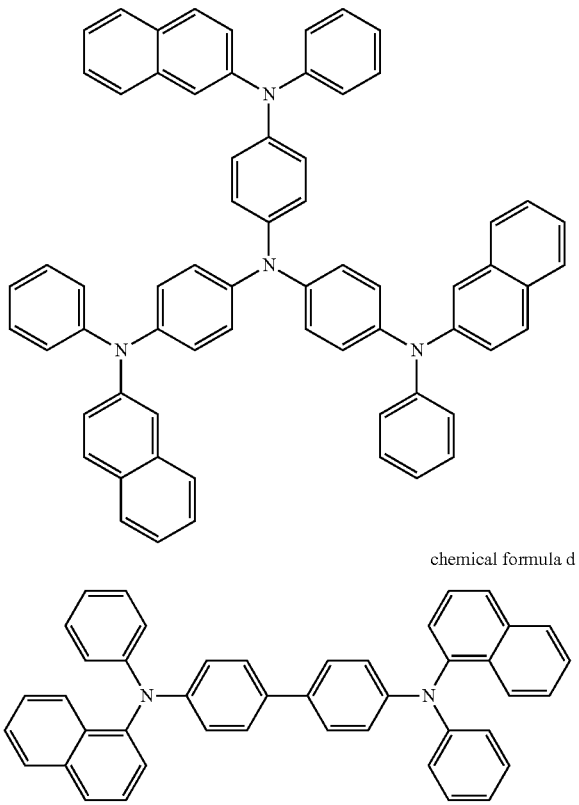

chemical formula c chemical formula d

A 15 Ω/cm² (1000 Å) ITO glass substrate from Corning Co. was cut into a size of 50 mm*50 mm*0.7 mm, and then under the irradiation of microwave, washed in acetone, isopropanol, purified water in turn for 15 minutes respectively, and then further washed in UV for 30 minutes. A hole injection layer was formed by vacuum depositing 2-TNATA to a thickness of 80 nm on the substrate. A hole transport layer was formed by vacuum depositing α-NPD to a thickness of 30 nm on the hole injection layer. A light-emitting layer was formed by vacuum depositing a compound represented by chemical formula a and a compound represented by chemical formula b (at a doping ratio of 8%) to a thickness of 30 nm on the hole transport layer. An electron transport layer was formed by vacuum depositing $Alq_3$ to a thickness of 30 nm on the light-emitting layer. On the electron transport layer, 0.5 nm LiF (electron injection) and 60 nm Al were vacuum depositing in turn, thereby an organic luminescent device was produced. In this comparative example 1 and the following application examples 1 to 24, vacuum deposition was carried out by using an EL deposition machine manufactured by DOV Co., Korean.

Application Examples 1-24

The organic luminescent devices having following structures were produced by using the process in comparative example 1, with the exception that the compounds 1 to 24 shown in the preparation examples were used as the light-emitting layer compound instead of the compound a. The organic luminescent devices having the structure of ITO/2-TNATA (80 nm)/α-NPD (30 nm)/indoloacridine-containing derivatives 1 to 24+compound b] (25 nm, content of b therein being 8.0%)/$Alq_3$(30 nm)/LiF(0.5 nm)/Al(60 nm).

Testing Example 1: The Tests for the Luminescence Properties of the Comparative Sample and the Samples 1-24

The comparative sample and the samples 1 to 24 were tested for evaluating the driving voltage, luminance, luminous efficiency and luminous color by using Keithley 2400 series digital source apparatus from the Taiwan Branch of American Keithley Instruments Inc., konica minolta CS-2000 from Konica Minolta, and CS-2000A photometer. The comparative sample and the samples 1 to 24 were subjected to the same tests. The results were listed in Table 3:

TABLE 3

| Compound No | Host material | Doping material | Driving voltage [V] | Luminance [cd/m2] | Luminous efficiency [cd/A] | Wavelength of luminescence [nm] |
|---|---|---|---|---|---|---|
| Com. Ex. 1 | a | b | 9.8 | 667 | 6.6 | 636 |
| 1 | 1 | b | 8.2 | 829 | 8.1 | 632 |
| 2 | 2 | b | 7.5 | 820 | 8.2 | 636 |
| 3 | 3 | b | 7.6 | 765 | 7.6 | 640 |
| 4 | 4 | b | 7.2 | 789 | 7.8 | 636 |
| 5 | 5 | b | 8.7 | 838 | 8.2 | 640 |
| 6 | 6 | b | 8.5 | 872 | 8.7 | 640 |
| 7 | 7 | b | 8.2 | 901 | 9.1 | 636 |
| 8 | 8 | b | 8.6 | 922 | 9.0 | 632 |
| 9 | 9 | b | 8.8 | 938 | 8.9 | 632 |
| 10 | 10 | b | 8.0 | 901 | 9.1 | 640 |
| 11 | 11 | b | 8.0 | 886 | 8.5 | 636 |
| 12 | 12 | b | 7.9 | 847 | 8.6 | 636 |
| 13 | 13 | b | 7.7 | 835 | 8.6 | 636 |
| 14 | 14 | b | 8.6 | 898 | 8.8 | 632 |
| 15 | 15 | b | 8.3 | 847 | 8.5 | 632 |
| 16 | 16 | b | 8.0 | 852 | 8.5 | 640 |
| 17 | 17 | b | 7.8 | 809 | 8.4 | 640 |
| 18 | 18 | b | 8.3 | 843 | 8.4 | 640 |
| 19 | 19 | b | 8.8 | 935 | 9.1 | 636 |
| 20 | 20 | b | 7.7 | 944 | 9.0 | 632 |
| 21 | 21 | b | 7.9 | 920 | 9.3 | 640 |
| 22 | 22 | b | 8.3 | 875 | 8.9 | 636 |

TABLE 3-continued

| Compound No | Host material | Doping material | Driving voltage [V] | Luminance [cd/m2] | Luminous efficiency [cd/A] | Wavelength of luminescence [nm] |
|---|---|---|---|---|---|---|
| 23 | 23 | b | 7.6 | 836 | 8.6 | 632 |
| 24 | 24 | b | 8.2 | 842 | 8.4 | 640 |

As shown in Table 3, the lights emitted from the samples mentioned above were in a wavelength range of from 632 to 640 nm, showing a color of red. As compared with the sample of the comparative example 1, the samples of the application examples 1 to 24 had significantly higher luminous efficiency.

Testing Example 2: Evaluation of the Lifetime Characteristics of the Sample of the Comparative Example 1 and Samples of the Application Examples 1 to 24

A lifetime testing apparatus LTS-1004AC of ENC Co. was used for the samples produced in the above-mentioned comparative example 1 and application examples 1 to 24, wherein lifetime of each sample was measured when 97% was reached by using 3000 nit as the standard. The results were shown in Table 4.

TABLE 4

| Sample No. | Host compound | Doping compound | Lifetime [h] |
|---|---|---|---|
| Com. Ex. 1 | a | b | 72 |
| 1 | 1 | b | 160 |
| 2 | 2 | b | 158 |
| 3 | 3 | b | 195 |
| 4 | 4 | b | 110 |
| 5 | 5 | b | 118 |
| 6 | 6 | b | 99 |
| 7 | 7 | b | 100 |
| 8 | 8 | b | 178 |
| 9 | 9 | b | 148 |
| 10 | 10 | b | 170 |
| 11 | 11 | b | 135 |
| 12 | 12 | b | 136 |
| 13 | 13 | b | 199 |
| 14 | 14 | b | 186 |
| 15 | 15 | b | 177 |
| 16 | 16 | b | 165 |
| 17 | 17 | b | 99 |
| 18 | 18 | b | 166 |
| 19 | 19 | b | 115 |
| 20 | 20 | b | 111 |
| 21 | 21 | b | 96 |
| 22 | 22 | b | 103 |
| 23 | 23 | b | 108 |
| 24 | 24 | b | 101 |

It can be confirmed from Table 4 that as compared with the sample of the comparative example 1, the samples of the application examples 1 to 24 have a longer luminescence lifetime.

In addition, organic luminescent devices having a structure of ITO/2-TNATA (80 nm)+indoloacridine-containing derivatives 1 to 24/α-NPD (30 nm)/compound a (30 nm, where b content was 8%)/Alq$_3$ (30 nm)/LiF (0.5 nm)/Al (60 nm) were prepared by using the process of comparative example 1, with the exception that the compounds 1 to 24 shown in the preparation examples were used as a hole injection material instead of the compound c. That is, these compounds 1-24 may be used as a hole-injecting material.

Organic luminescent devices having a structure of ITO/2-TNATA (80 nm)/indoloacridine-containing derivatives 1 to 24+α-NPD (30 nm)/compound a+compound b (25 nm, where b content was 8.0%)/Alq$_3$ (30 nm)/LiF (0.5 nm)/Al (60 nm) were prepared by using the process of comparative example 1, with the exception that the compounds 1 to 24 shown in the preparation examples, which may used as a hole-transporting material, were used for the compound for the hole transporting layer instead of the compound d.

Although the present invention has been specifically described and illustrated by using exemplary embodiments, it should be understood that those of ordinary skill may take various changes in form and details without departing from the spirit and scope of the invention as defined by the following claims.

What is claimed is:

1. An indoloacridine-containing derivative represented by the following molecular structural formula (I):

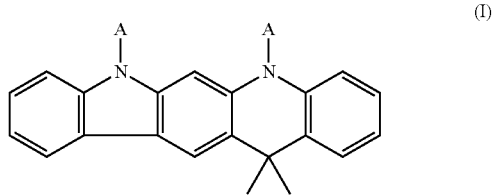

(I)

wherein A is a group represented by the formula (II):

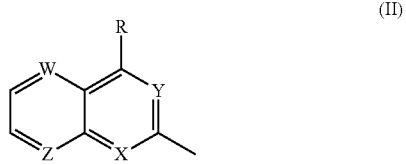

(II)

wherein X, Y, Z and W represent a carbon atom or a nitrogen atom, and at least one of W, X, Y and Z represents a nitrogen atom; and
wherein R represents a phenyl group, a biphenylyl group, a naphthyl group or a phenanthryl group.

2. The indoloacridine-containing derivative according to claim 1, wherein X represents a nitrogen atom.

3. The indoloacridine-containing derivative according to claim 2, wherein X and Y represent a nitrogen atom.

4. The indoloacridine-containing derivative according to claim 3, wherein X, Y and Z represent a nitrogen atom.

5. The indoloacridine-containing derivative according to claim 4, wherein X, Y, Z and W represent a nitrogen atom.

6. The indoloacridine-containing derivative according to claim 1, wherein R represents phenyl, 1-naphthyl, 2-naphthyl, 4-biphenylyl, 3-biphenylyl or 9-phenanthryl.

7. The indoloacridine-containing derivative according to claim 1, wherein the indoloacridine-containing derivative is any one selected from the compounds represented by the following chemical structural formulae (1) to (24):

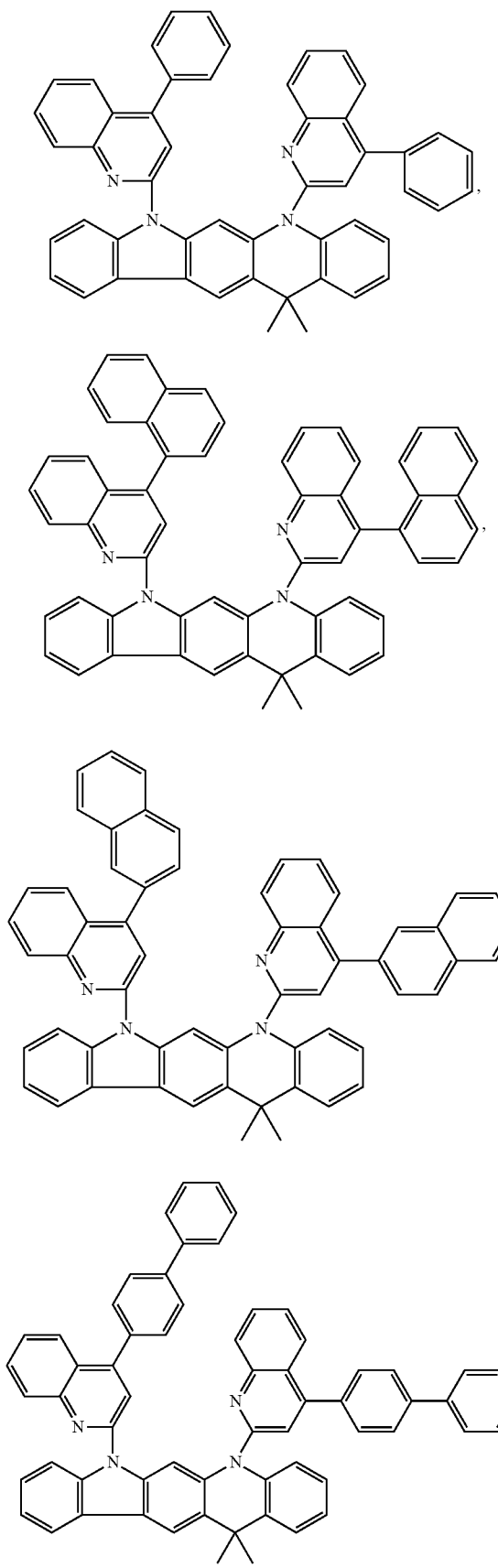
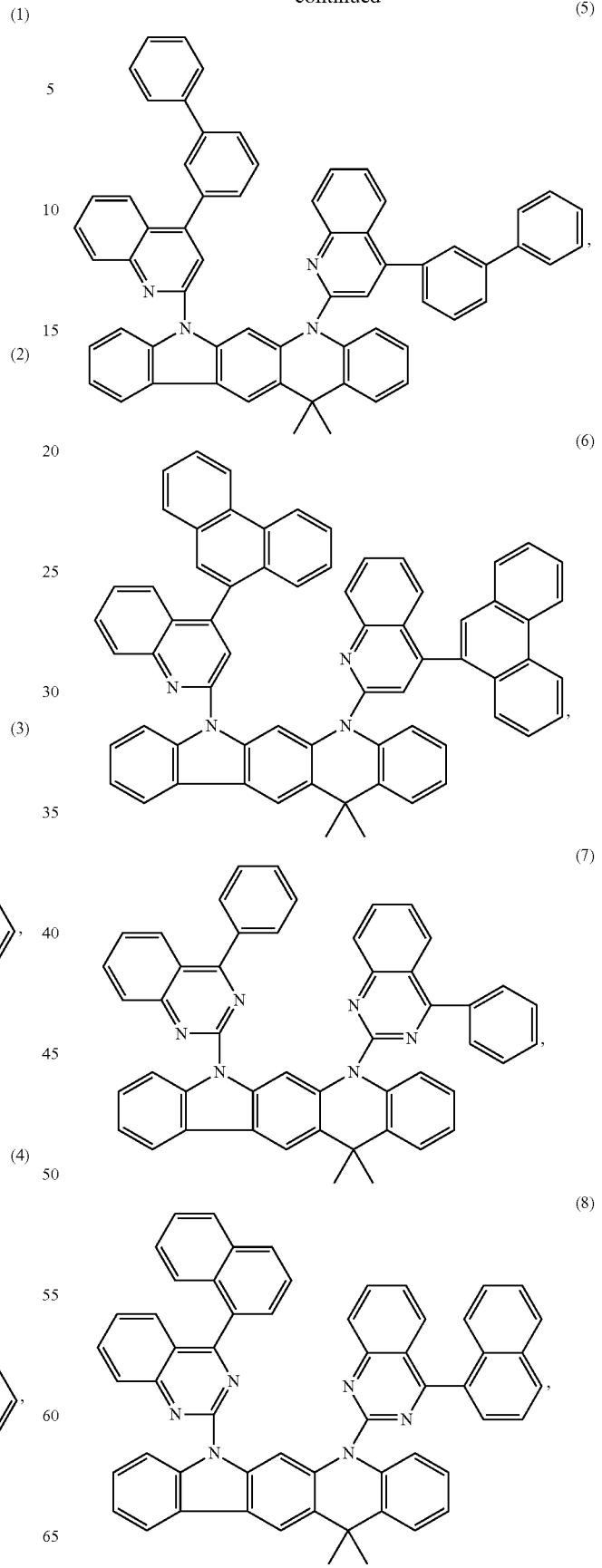

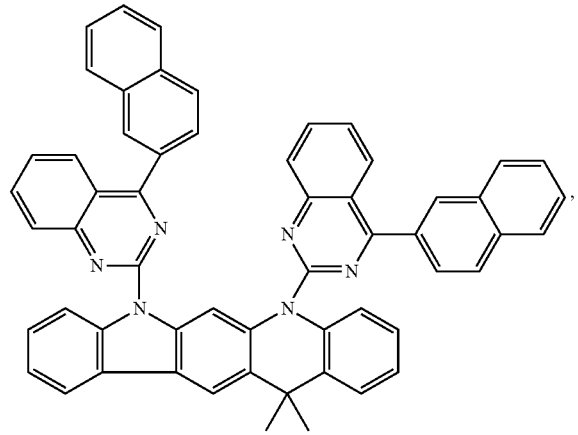
(9)
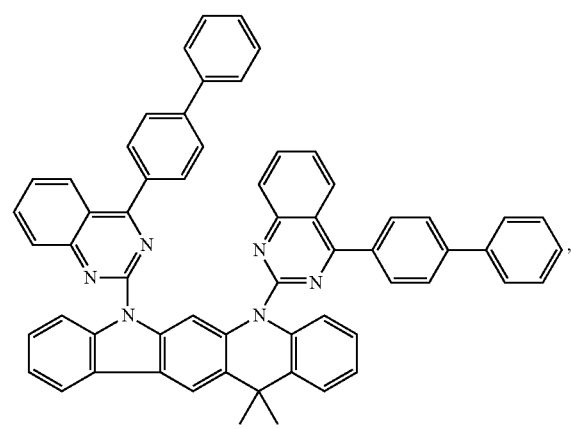
(10)
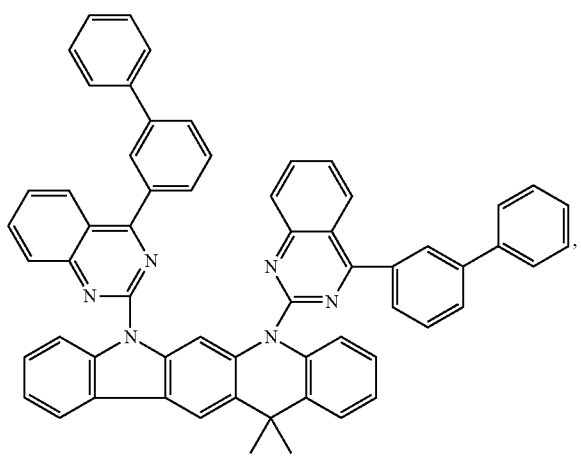
(11)
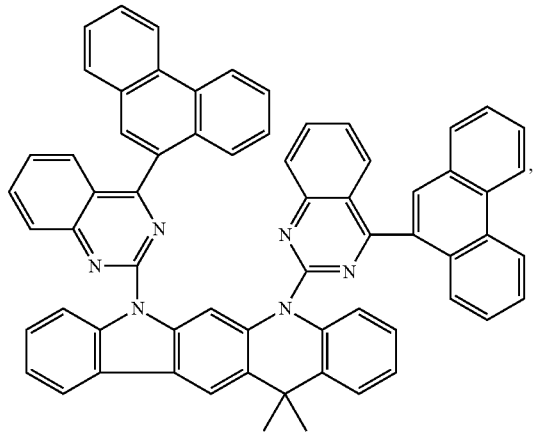
(12)
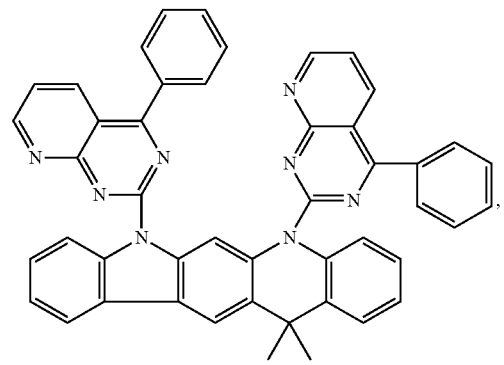
(13)
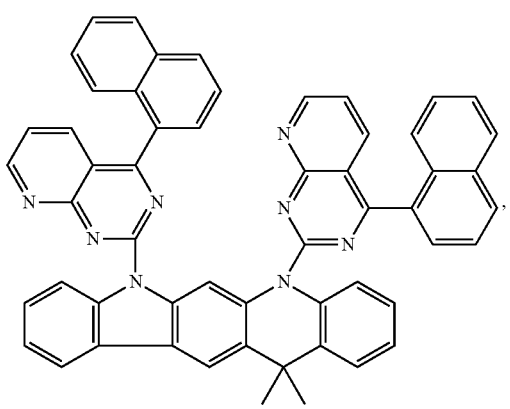
(14)
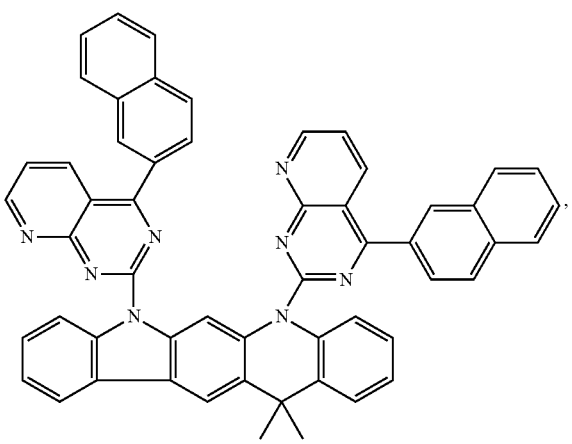
(15)

-continued
(16)
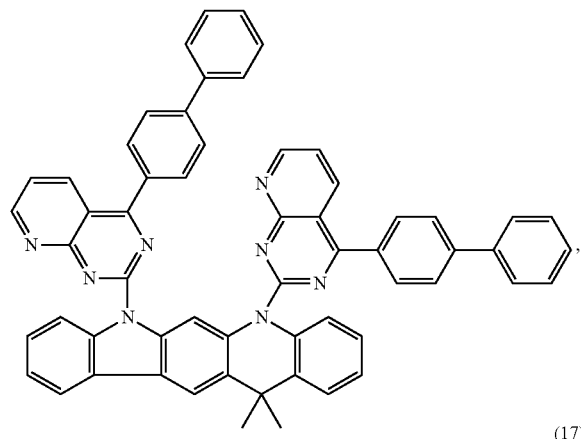
(17)
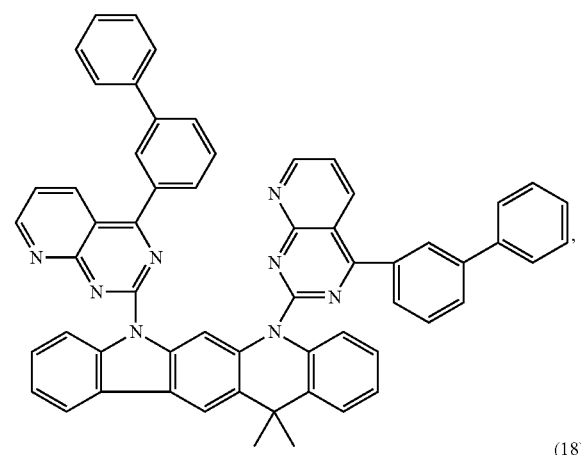
(18)
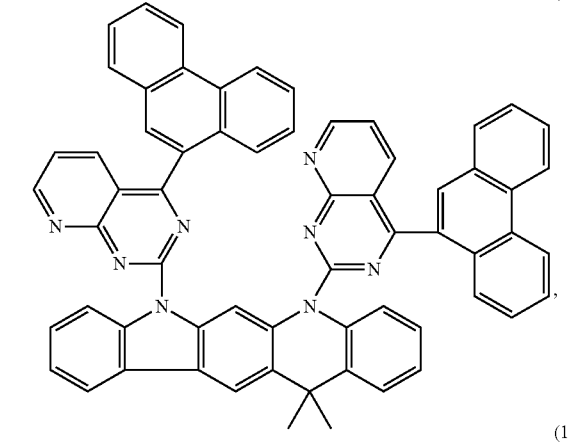
(19)
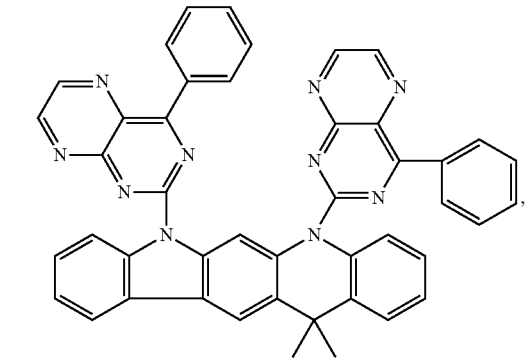
-continued
(20)
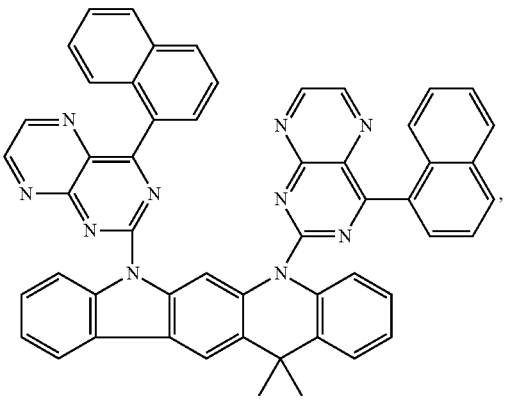
(21)
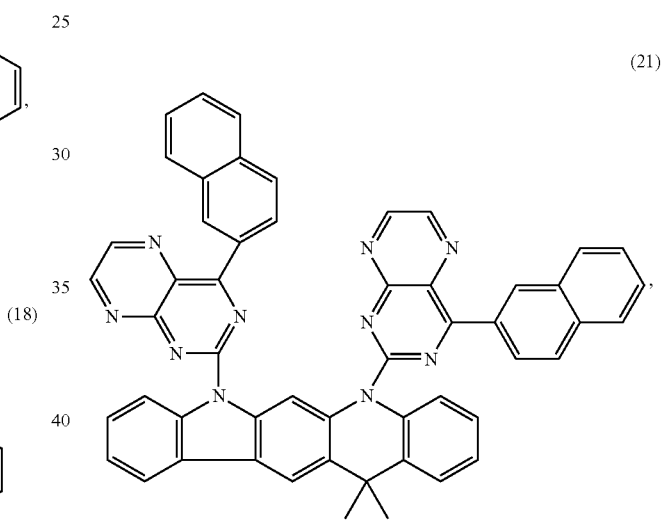
(22)
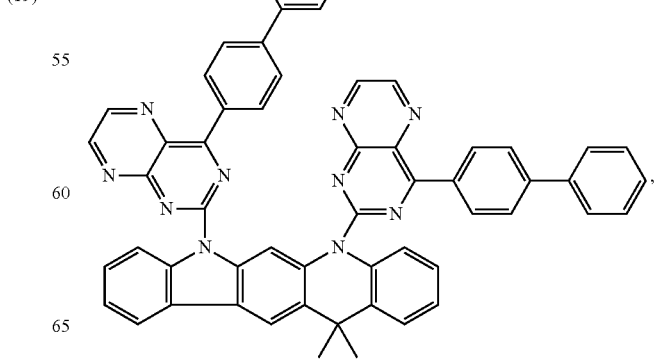

-continued

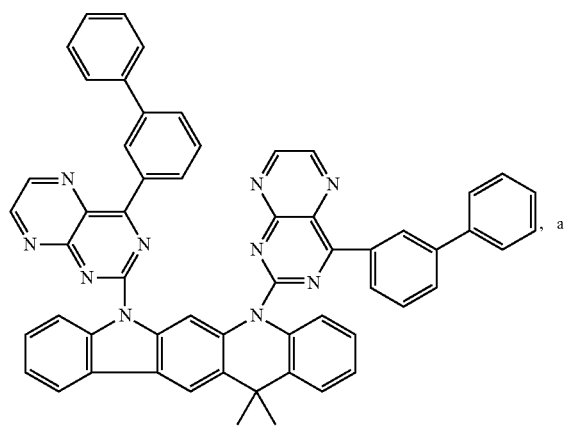, and

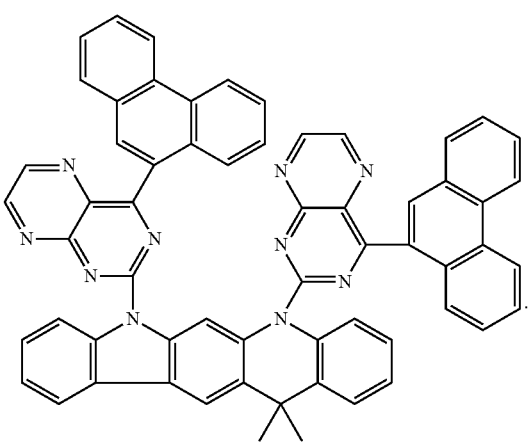.

8. A process for preparing the compound of claim 1, comprising a step of reacting a compound represented by formula (III)

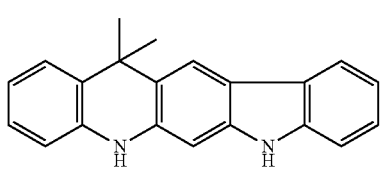

with a compound represented by formula (IV)

(IV)

wherein R, X, Y, Z and W have the same definitions as those in claim 1,
wherein the process comprises the following Steps S1 to S3:
Step S1: adding the compound represented by formula (III), the compound represented by formula (IV), potassium hydroxide, copper iodide and a solvent into a degassed reaction container;
Step S2: increasing a reaction temperature and refluxing, allowing the reaction to be carried out; and
Step S3: performing filtration, washing and recrystallization to obtain the indoloacridine-containing derivative represented by formula (I).

9. The process according to claim 8, wherein the process further comprises performing the following Steps M1 to M5 to produce the compound represented by formula (III):
Step M1: reacting 9,10-dihydro-9,9-dimethylacridine with solid triphosgene to obtain a compound represented by formula (V):

(V)

Step M2: reacting the compound represented by formula (V) with N-bromosuccinimide to obtain a compound represented by formula (VI):

Step M3: reacting the compound represented by formula (VI) with 2-chloroaniline to obtain a compound represented by formula (VII):

(VII)

Step M4: reacting the compound represented by formula (VII) in the presence of palladium acetate, di-tert-butyl methylphosphonium tetraphenylborate and cesium carbonate, to obtain a compound represented by formula (VIII):

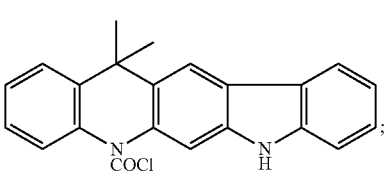

Step M5: removing the chloroformyl protection of the compound represented by formula (VIII) to obtain the compound represented by formula (III).

10. The process according to claim 8, wherein the process further comprises producing the compound represented by formula (IV) by reacting R—B(OH)$_2$ with a compound represented by formula (IX):

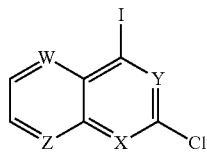

(IX)

wherein R, X, Y, Z and W have the same definitions as those in claim 1.

11. The process according to claim 10, wherein the compound represented by formula (IV) is obtained by the following Steps N1 to N3:

Step N1: adding the compound represented by formula (IX), R—B(OH)$_2$, potassium carbonate and a solvent into a degassed reaction container;

Step N2: refluxing, and allowing the reaction to be carried out sufficiently;

Step N3: performing extraction, washing, drying and purification with column chromatography, to obtain the compound represented by formula (IV).

12. An organic electroluminescent device, comprising a first electrode, a second electrode and one or more organic compound layer(s) provided between the first electrode and the second electrode, wherein at least one of the organic compound layers comprises at least one indoloacridine-containing derivative according to claim 1.

13. The organic electroluminescent device according to claim 12, wherein the indoloacridine-containing derivative is a phosphorescence host material.

14. The organic electroluminescent device according to claim 13, wherein the indoloacridine-containing derivative is a red phosphorescence host material.

\* \* \* \* \*

UNITED STATES PATENT AND TRADEMARK OFFICE
CERTIFICATE OF CORRECTION

| | |
|---|---|
| PATENT NO. | : 9,676,767 B2 |
| APPLICATION NO. | : 14/425254 |
| DATED | : June 13, 2017 |
| INVENTOR(S) | : Wenyu Ma, Xiaoyu Ma and Na Li |

It is certified that error appears in the above-identified patent and that said Letters Patent is hereby corrected as shown below:

In the Specification

Column 18, Line 26:
Delete "8-hydroxyquinoline"
Insert --8-hydroxylquinoline--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*